United States Patent
Thompson et al.

(10) Patent No.: US 7,955,369 B2
(45) Date of Patent: Jun. 7, 2011

(54) SYSTEMS AND METHODS FOR TREATING A HOLLOW ANATOMICAL STRUCTURE

(75) Inventors: Russell Blake Thompson, Los Altos, CA (US); Fiona Maria Sander, Los Altos Hills, CA (US); Vijay Kumar Dhaka, Boston, MA (US); Brady David Esch, San Jose, CA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/206,649

(22) Filed: Sep. 8, 2008

(65) Prior Publication Data
US 2009/0149932 A1    Jun. 11, 2009

Related U.S. Application Data

(63) Continuation of application No. 11/236,316, filed on Sep. 27, 2005, now abandoned.

(60) Provisional application No. 60/613,415, filed on Sep. 27, 2004, provisional application No. 60/701,303, filed on Jul. 21, 2005.

(51) Int. Cl.
*A61F 7/12* (2006.01)
(52) U.S. Cl. .......................................... 607/113; 607/96
(58) Field of Classification Search .............. 606/32–50; 607/96, 113
See application file for complete search history.

(56) References Cited

U.S. PATENT DOCUMENTS

| | | | |
|---|---|---|---|
| 4,765,331 | A | 8/1988 | Petrazzi et al. |
| 4,907,589 | A | 3/1990 | Cosman |
| 5,100,388 | A | 3/1992 | Behl et al. |
| 5,188,602 | A | 2/1993 | Nichols |

(Continued)

FOREIGN PATENT DOCUMENTS

EP    1350481 A2    4/2003

(Continued)

OTHER PUBLICATIONS

VNUS Closure(tm) Catheter—Instructions for Use with drawings of Closure(tm) catheter. The depicted catheter, with the instructions for use enclosed, was on sale in the United States more than on year before the earliest effective priority date for the present application.

(Continued)

*Primary Examiner* — Michael Peffley
*Assistant Examiner* — Ronald Hupczey, Jr.
(74) *Attorney, Agent, or Firm* — Knobbe, Martens, Olson & Bear, LLP

(57) ABSTRACT

A catheter includes multiple primary leads to deliver energy for ligating a hollow anatomical structure. Each of the primary leads includes a resistive element located at the working end of the catheter. Separation is maintained between the leads such that each lead can individually receive power. The catheter can include a lumen to accommodate a guide wire or to allow fluid delivery. Energy is applied until the diameter of the hollow anatomical structure is reduced to the point where occlusion is achieved. In one embodiment, a balloon is inflated to place the resistive elements into apposition with a hollow anatomical structure and to occlude the structure before the application of energy. The inflated balloon impairs blood flow and facilitates the infusion of saline, or medication, to the hollow anatomical structure in order to reduce the occurrence of coagulation and to improve the heating of the structure by the catheter.

27 Claims, 43 Drawing Sheets

U.S. PATENT DOCUMENTS

| | | | |
|---|---|---|---|
| 5,441,516 A | 8/1995 | Wang et al. | |
| 5,584,830 A | 12/1996 | Ladd et al. | |
| 5,588,432 A | 12/1996 | Crowley | |
| 5,611,778 A | 3/1997 | Brinon | |
| 5,743,903 A | 4/1998 | Stern et al. | |
| 5,746,224 A | 5/1998 | Edwards | |
| 5,797,905 A | 8/1998 | Fleischman et al. | |
| 5,837,003 A * | 11/1998 | Ginsburg | 607/106 |
| 5,843,152 A | 12/1998 | Tu et al. | |
| 5,851,210 A | 12/1998 | Torossian | |
| 5,860,923 A | 1/1999 | Lenker | |
| 5,931,835 A | 8/1999 | Mackey | |
| 5,954,717 A | 9/1999 | Behl et al. | |
| 6,010,500 A | 1/2000 | Sherman et al. | |
| 6,033,398 A | 3/2000 | Farley et al. | |
| 6,041,260 A | 3/2000 | Stern et al. | |
| 6,183,468 B1 | 2/2001 | Swanson et al. | |
| 6,217,573 B1 | 4/2001 | Webster | |
| 6,258,084 B1 | 7/2001 | Goldman et al. | |
| 6,290,715 B1 | 9/2001 | Sharkey et al. | |
| 6,304,776 B1 | 10/2001 | Muntermann | |
| 6,322,559 B1 | 11/2001 | Daulton et al. | |
| 6,327,505 B1 * | 12/2001 | Medhkour et al. | 607/99 |
| 6,355,033 B1 | 3/2002 | Moorman et al. | |
| 6,391,024 B1 | 5/2002 | Sun et al. | |
| 6,408,199 B1 | 6/2002 | Goldin | |
| 6,490,488 B1 | 12/2002 | Rudie et al. | |
| 6,517,534 B1 | 2/2003 | McGovern et al. | |
| 6,539,265 B2 | 3/2003 | Medhkour et al. | |
| 6,605,084 B2 | 8/2003 | Acker et al. | |
| 6,723,094 B1 | 4/2004 | Desinger | |
| 6,905,494 B2 | 6/2005 | Yon et al. | |
| 7,276,061 B2 * | 10/2007 | Schaer et al. | 607/41 |
| 7,364,577 B2 | 4/2008 | Wham et al. | |
| 7,524,316 B2 * | 4/2009 | Hennings et al. | 606/7 |
| 2002/0177846 A1 * | 11/2002 | Mulier et al. | 606/27 |
| 2003/0078569 A1 | 4/2003 | Caldera | |
| 2003/0191460 A1 | 10/2003 | Hobbs et al. | |
| 2004/0010289 A1 | 1/2004 | Biggs et al. | |
| 2004/0122420 A1 | 6/2004 | Amoah | |
| 2004/0199151 A1 | 10/2004 | Neuberger | |
| 2005/0085804 A1 | 4/2005 | McGaffigan | |
| 2005/0192654 A1 | 9/2005 | Chanduszko et al. | |
| 2006/0142824 A1 | 6/2006 | Zikorus et al. | |
| 2007/0049999 A1 | 3/2007 | Esch et al. | |
| 2007/0050000 A1 | 3/2007 | Esch et al. | |
| 2007/0055326 A1 | 3/2007 | Farley et al. | |
| 2007/0055327 A1 | 3/2007 | Esch et al. | |
| 2007/0100405 A1 | 5/2007 | Thompson et al. | |
| 2007/0179575 A1 | 8/2007 | Esch et al. | |

FOREIGN PATENT DOCUMENTS

| | | |
|---|---|---|
| EP | 1527748 A | 5/2005 |
| WO | WO 93/08755 A | 5/1993 |
| WO | WO 98/55046 A | 12/1998 |
| WO | WO 99/11185 A | 3/1999 |
| WO | WO 2004/093693 A1 | 11/2004 |
| WO | WO 2005/034783 A | 4/2005 |
| WO | WO 2006/054170 A1 | 5/2006 |
| WO | WO 2006/069313 A | 6/2006 |

OTHER PUBLICATIONS

International Search Report for Application No. PCT-US2006-028454 mailed Mar. 28, 2007.

Avitall et al, "The Effects of Electrode-Tissue Contact on Radiofrequency Lesion Generation", Dec. 1997, PACE, vol. 20, 2899-2910.

Cao et al, "Using Electrical Impedance to Predict Catheter-Endocardial Contact During RF Cardiac Ablation", Mar. 2002, IEEE Transactions on Biomedical Engineering, vol. 49 No. 3, 247-252.

Zheng et al, "Electrode Impedance: An Indicator of Electrode-Tissue Contact and Lesion Dimensions During Linear Ablation", 2000, Journal of Interventional Cardiac Electrophysiology, 645-654.

U.S. Appl. No. 12/686,323, filed Jan. 12, 2010, Thompson et al.

U.S. Appl. No. 12/691,703, filed Jan. 21, 2010, Thompson et al.

Introducing Closure® Catheters with Graduation Marks. About Oct. 1999.

* cited by examiner

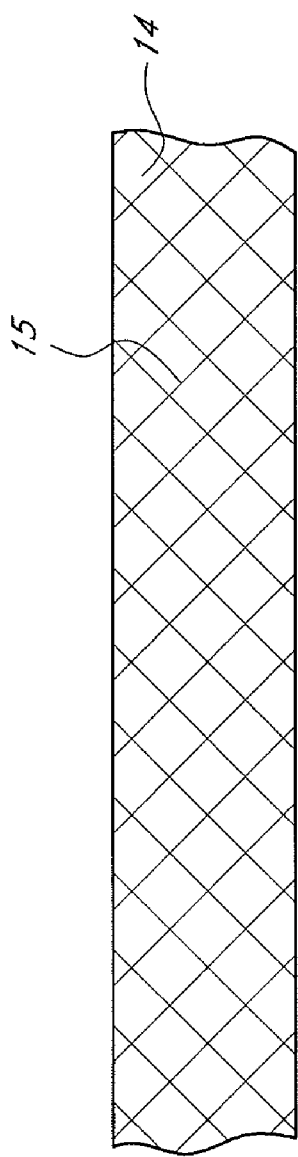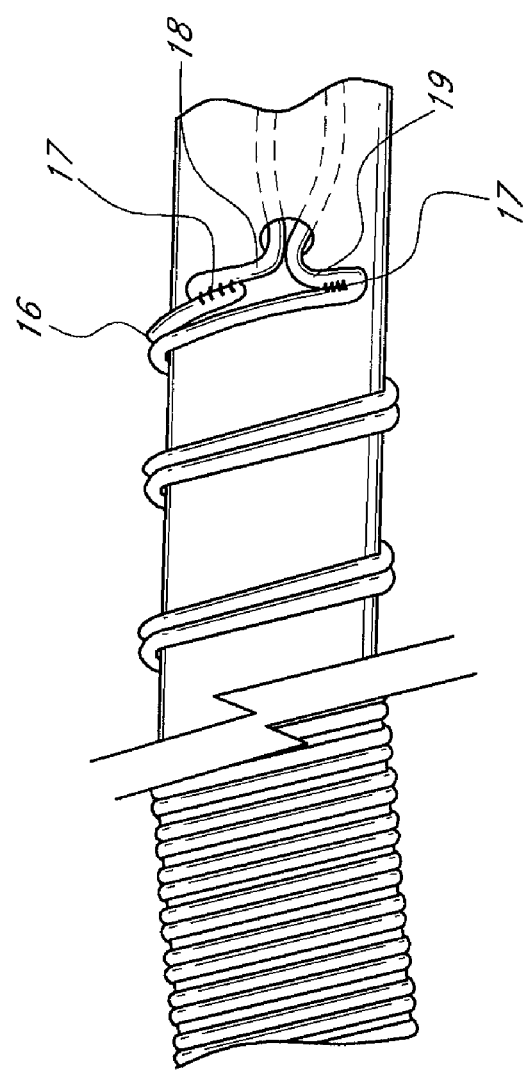
FIG. 5
FIG. 6

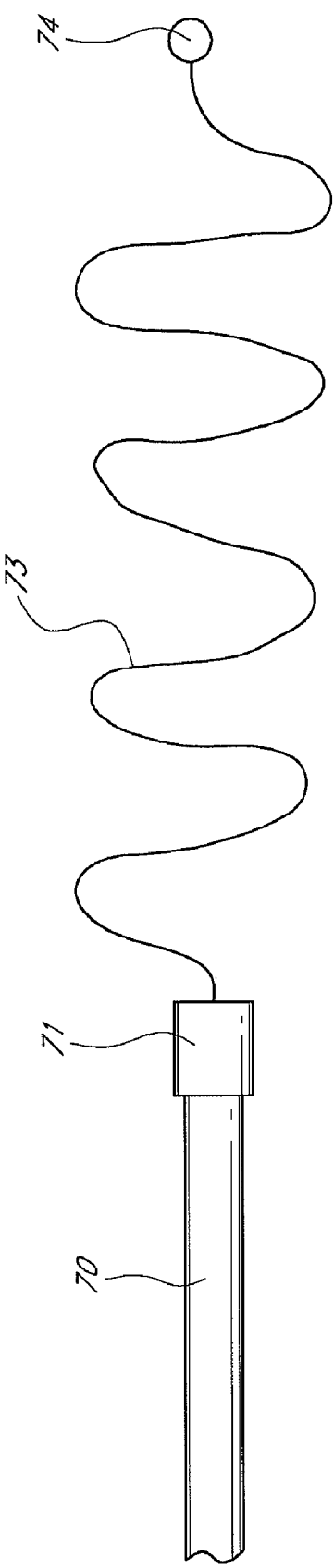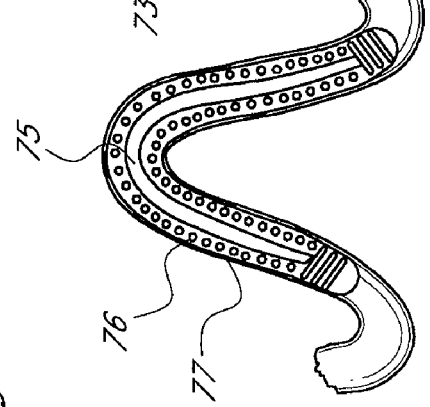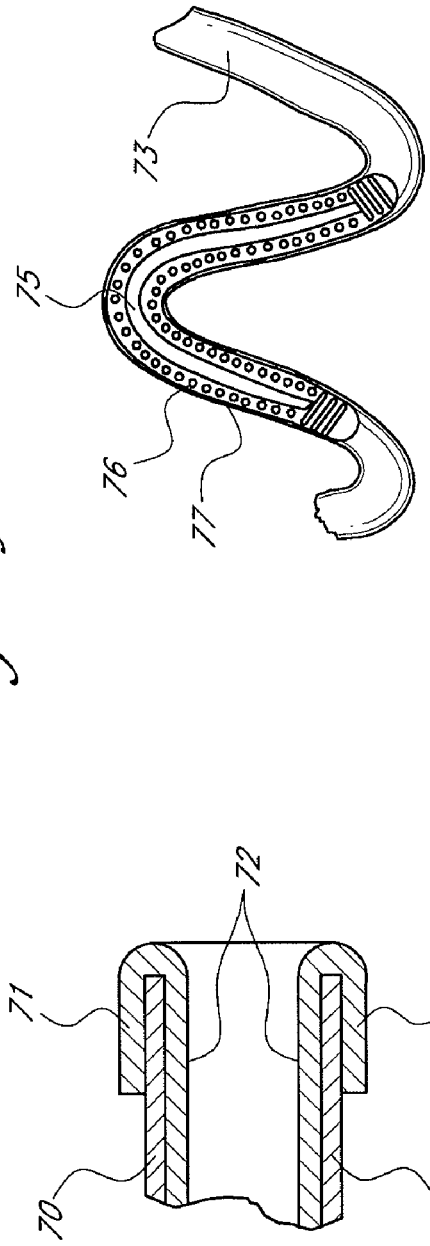
FIG. 10A
FIG. 10B
FIG. 10C

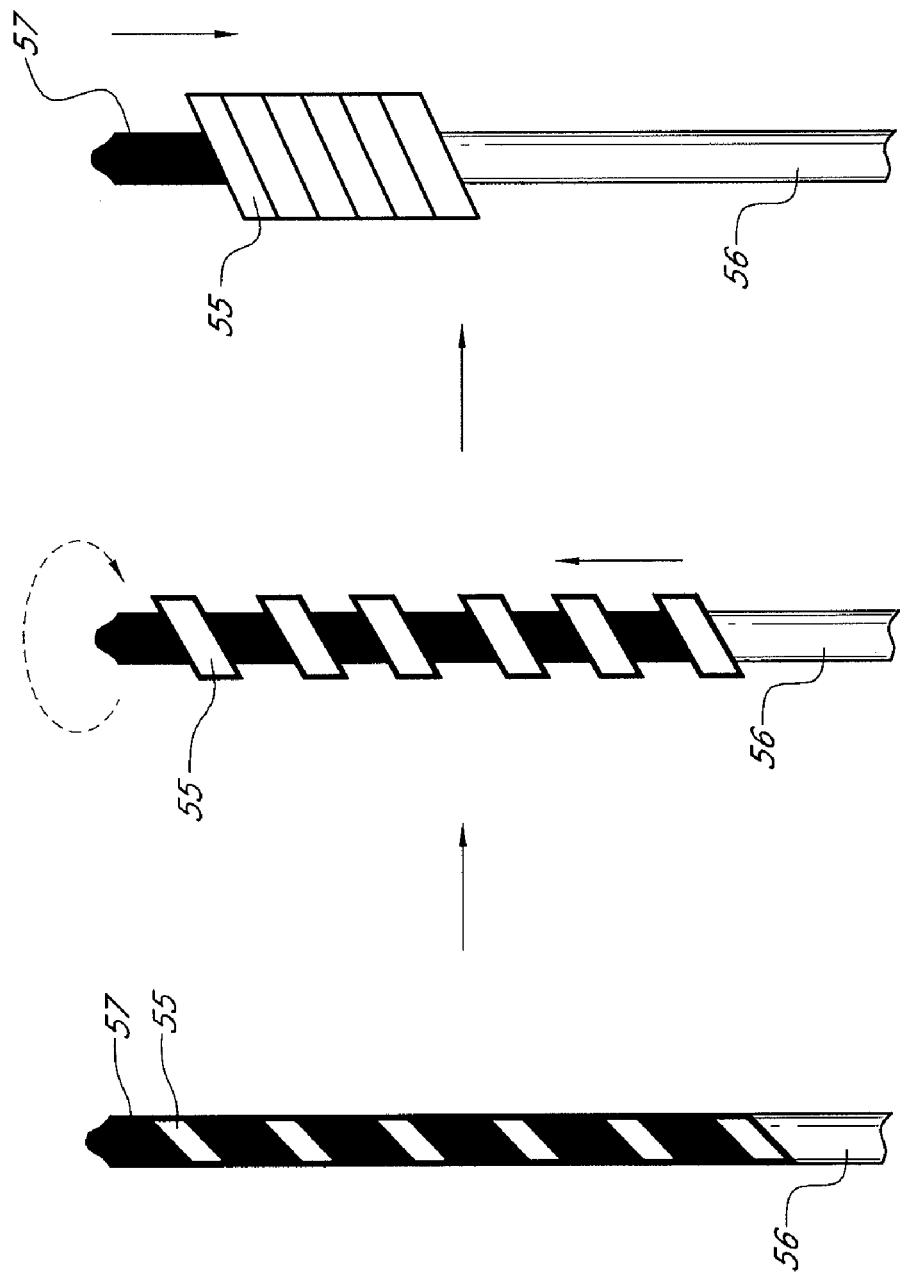

Device has an uneven insertion, does not butt up against the sheath completely

Outer sheath is adjusted to expose the full mark and locked in place

The Device is exposed by the Outer sheath adjustment amount. The Outer sheath can only move Device Distal.

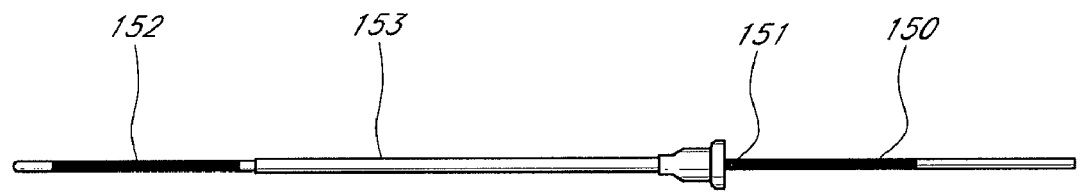
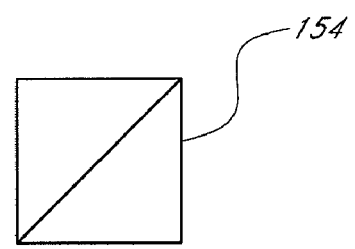
FIG. 26
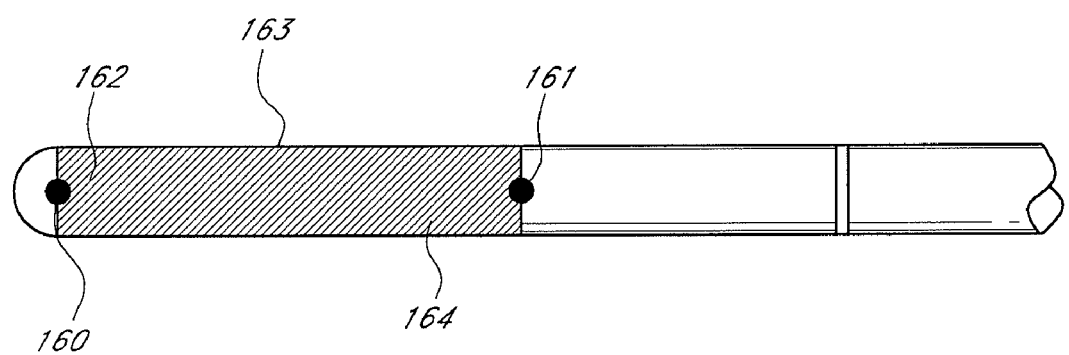
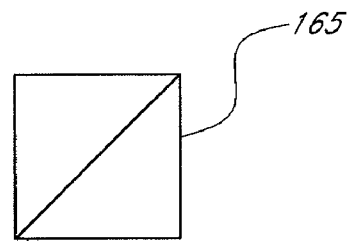
FIG. 27

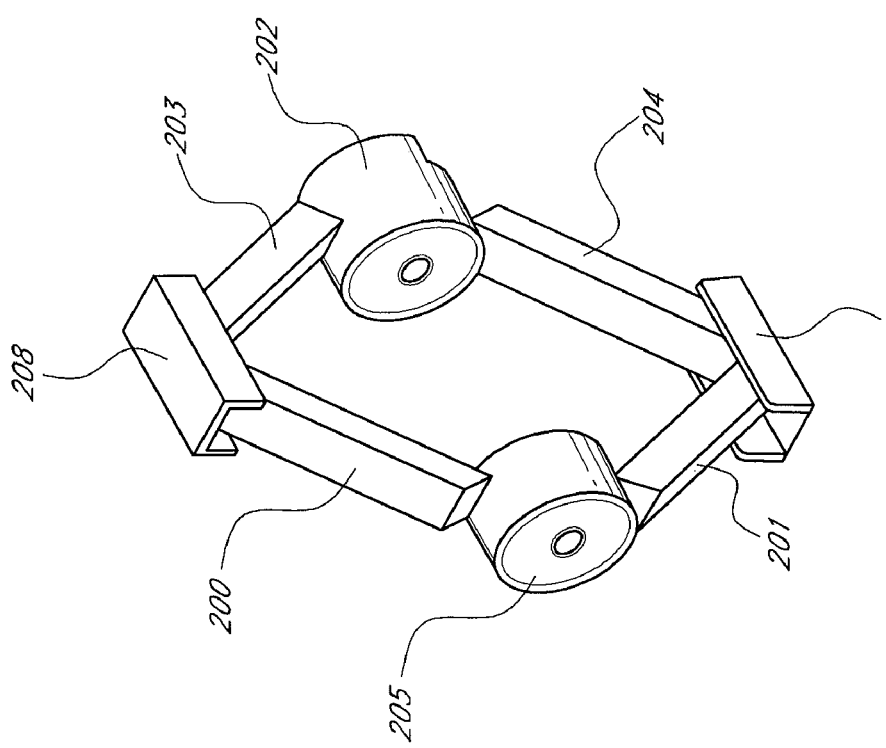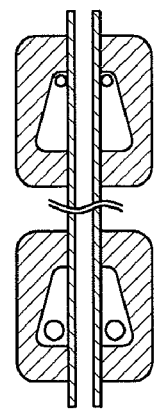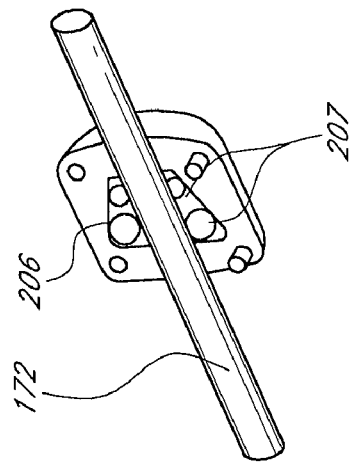
FIG. 31A
FIG. 31B

SYSTEMS AND METHODS FOR TREATING A HOLLOW ANATOMICAL STRUCTURE

RELATED APPLICATIONS

This application is a continuation of application Ser. No. 11/236,316 filed on Sep. 27, 2005, now abandoned, which claims the benefit of priority under 35 U.S.C. §119(e) of U.S. Provisional Application No. 60/613,415 filed on Sep. 27, 2004, and entitled "RESISTIVE ELEMENT SYSTEM," and U.S. Provisional Application No. 60/701,303 filed on Jul. 21, 2005, and entitled "RESISTIVE ELEMENT SYSTEM," the contents of which are hereby incorporated by reference in their entirety and are to be considered a part of this specification.

BACKGROUND OF THE INVENTION

Field of the Invention

The invention relates generally to a method and apparatus for applying energy to constrict and/or shrink a hollow anatomical structure such as a vein, and more particularly, a method and apparatus to conduct electrical current and/or heat to the wall of the hollow anatomical structure.

SUMMARY OF THE INVENTION

In one embodiment, a catheter comprises an elongate shaft and a resistive heating element located near the distal end of the elongate shaft. A temperature-sensing element is located in proximity to the resistive heating element, and may be centered along the length of the heating element, or offset from center. The resistive heating element may comprise a coil, and the coil may be of a constant pitch or of a varying pitch.

In one embodiment, a catheter comprises an elongate shaft and a resistive heating element located near the distal end of the elongate shaft. A sheath is slidably disposed on the shaft. The sheath and catheter are relatively moveable between a first configuration in which the sheath covers substantially all of the resistive heating element, and a second configuration in which the sheath covers less than substantially all of the resistive heating element. The resistive heating element may comprise a coil, and the coil may be of a constant pitch or of a varying pitch.

In another embodiment, a catheter system comprises an elongate shaft and an energy-emission element located near the distal end of the elongate shaft. The energy-emission element optionally includes a plurality of emission segments, and each of the segments is independently operable to emit energy into the surroundings of the energy-emission element. Optionally, the catheter system further comprises a power source drivingly connected to the emission segments. The power source is operable pursuant to a multiplexing algorithm to deliver power to, and operate, the emission segments in a multiplexed fashion. In one embodiment, the energy-emission element comprises a resistive element such as a resistive coil. In another embodiment, the energy-emission element comprises an RF emitter.

In another embodiment, a catheter system comprises an elongate shaft and an energy-emission element located distal of the elongate shaft. The energy-emission element has an effective axial length along which the energy-emission element emits energy. The effective axial length is adjustable.

In another embodiment, a catheter comprises an elongate shaft and an expandable shaft located on a distal portion of the elongate shaft. A number of heater elements are expandable by a balloon. The heater elements may have a wavy, sinusoidal or serpentine configuration.

BRIEF DESCRIPTION OF THE DRAWINGS

FIG. 5 illustrates a side view of another embodiment of the working end of the catheter of FIG. 3;

FIG. 6 illustrates a side view of yet another embodiment of the working end of the catheter of FIG. 3;

FIG. 10A-10C illustrate other embodiments of a working portion of the catheter body;

FIG. 12A illustrates an embodiment of the working portion of a catheter having a conformable helical electrode axially coiled on a shaft;

FIG. 12B illustrates the device of FIG. 12A being radially expanded by rotation of a distal catheter portion;

FIG. 12C illustrates the device of FIG. 12B expanded and compressed distally to remove inter coil gaps;

FIG. 16, which includes

FIG. 21, which includes

FIG. 24, which includes

FIG. 26 illustrates an exemplary embodiment of an indexing system having a temperature sensor.

FIG. 27 illustrates an exemplary embodiment of an indexing system having multiple temperature sensors.

FIG. 30, FIGS. 31A-31B, and FIGS. 32A and 32B illustrate exemplary embodiments of linkages usable to index a catheter by a certain amount.

DETAILED DESCRIPTION OF THE PREFERRED EMBODIMENTS

The features of the system and method will now be described with reference to the drawings summarized above. The drawings, associated descriptions, and specific implementation are provided to illustrate embodiments of the invention and not to limit the scope of the invention.

In addition, methods and functions described herein are not limited to any particular sequence, and the acts or states relating thereto can be performed in other sequences that are appropriate. For example, described acts or states may be performed in an order other than that specifically disclosed, or multiple acts or states may be combined in a single act or state.

Figure 1:
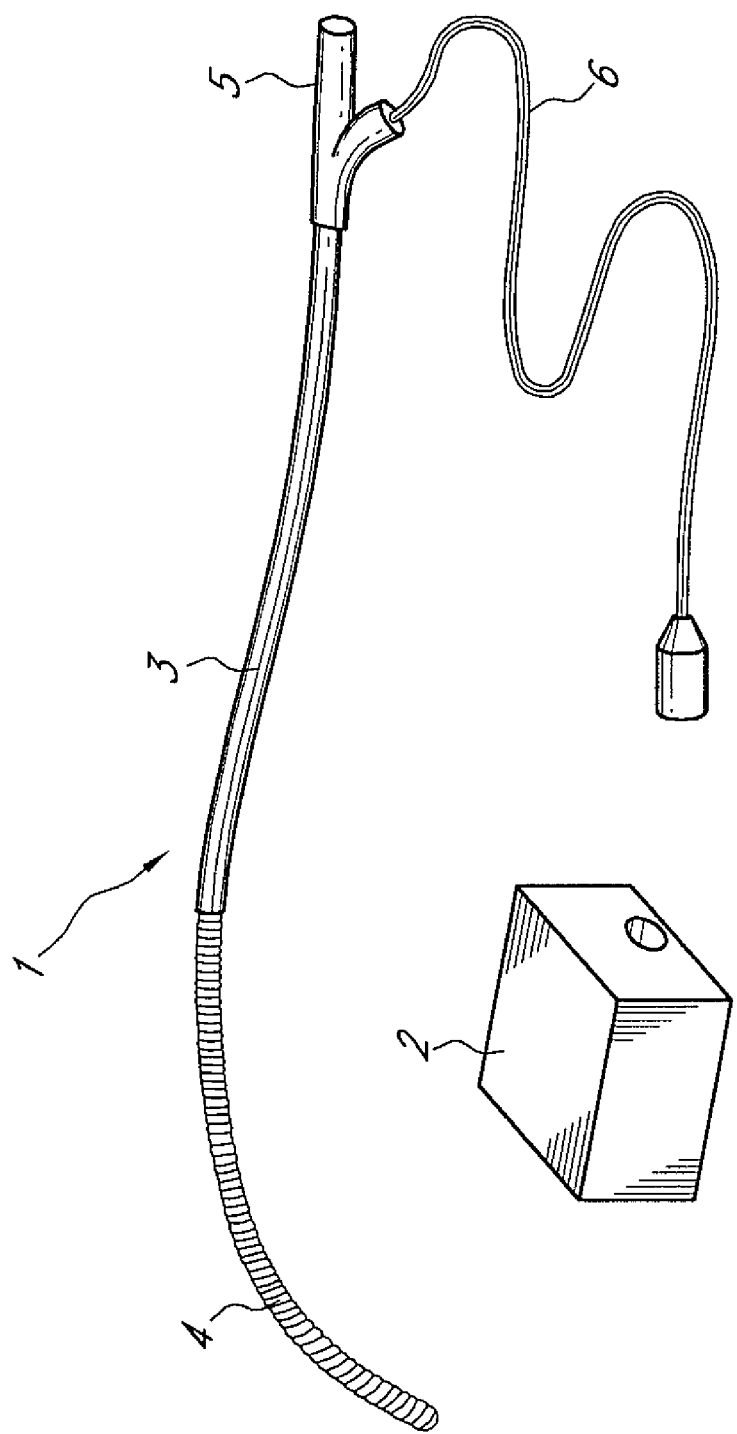
FIG. 1 illustrates an overall view of a resistive element system according to one embodiment.

FIG. 1 illustrates an embodiment of a resistive element system for applying energy to the wall of a hollow anatomical structure such as (but not limited to) the inner wall(s) of a vein, e.g. a greater saphenous vein or a varicose vein. As illustrated, the resistive element system comprises a catheter 1. The catheter 1 includes a catheter shaft 3, which may be used to maneuver the distal portion 4 of the catheter 1 during placement. In one embodiment, the catheter shaft 3 is comprised of a biocompatible material having a low coefficient of friction. For example, the shaft 3 may comprise a polyimide. In other embodiments, the shaft 3 may comprise PEEK, TEFLON®, HYTREL®, or any other such suitable material. In one embodiment, the catheter shaft 3 is sized to fit within a vascular structure that may be between 2 and 14 French, but preferably between 4 and 8 French, which corresponds to a diameter of between 1.3 mm (0.05 in) and 2.7 mm (0.10 in), or other sizes as appropriate. The distal portion 4 transfers energy (e.g. heat) directly to an inner vein wall. The proximal end of the catheter has a handle 5. The handle 5 includes a port for fluid and a connection 6 for interfacing with an energy source 2.

In one embodiment, an energy source 2 comprises an alternating current (AC) source, such as an RF generator. In other embodiments, the energy source 2 comprises a direct current (DC) power supply, such as, for example, a battery, a capacitor, or other energy source. The power source 2 may also incorporate a controller that, by use of a microprocessor, applies power using a temperature sensor (e.g. a thermocouple or a resistance temperature device) located in the working portion of the catheter 1. For example, the controller may heat the tissue of a hollow anatomical structure to a set temperature. In an alternate embodiment, the user selects a constant power output of the energy source 2. For example, the user may manually adjust the power output relative to the temperature display from the temperature sensor in the working portion of the catheter 1.

Figure 2:
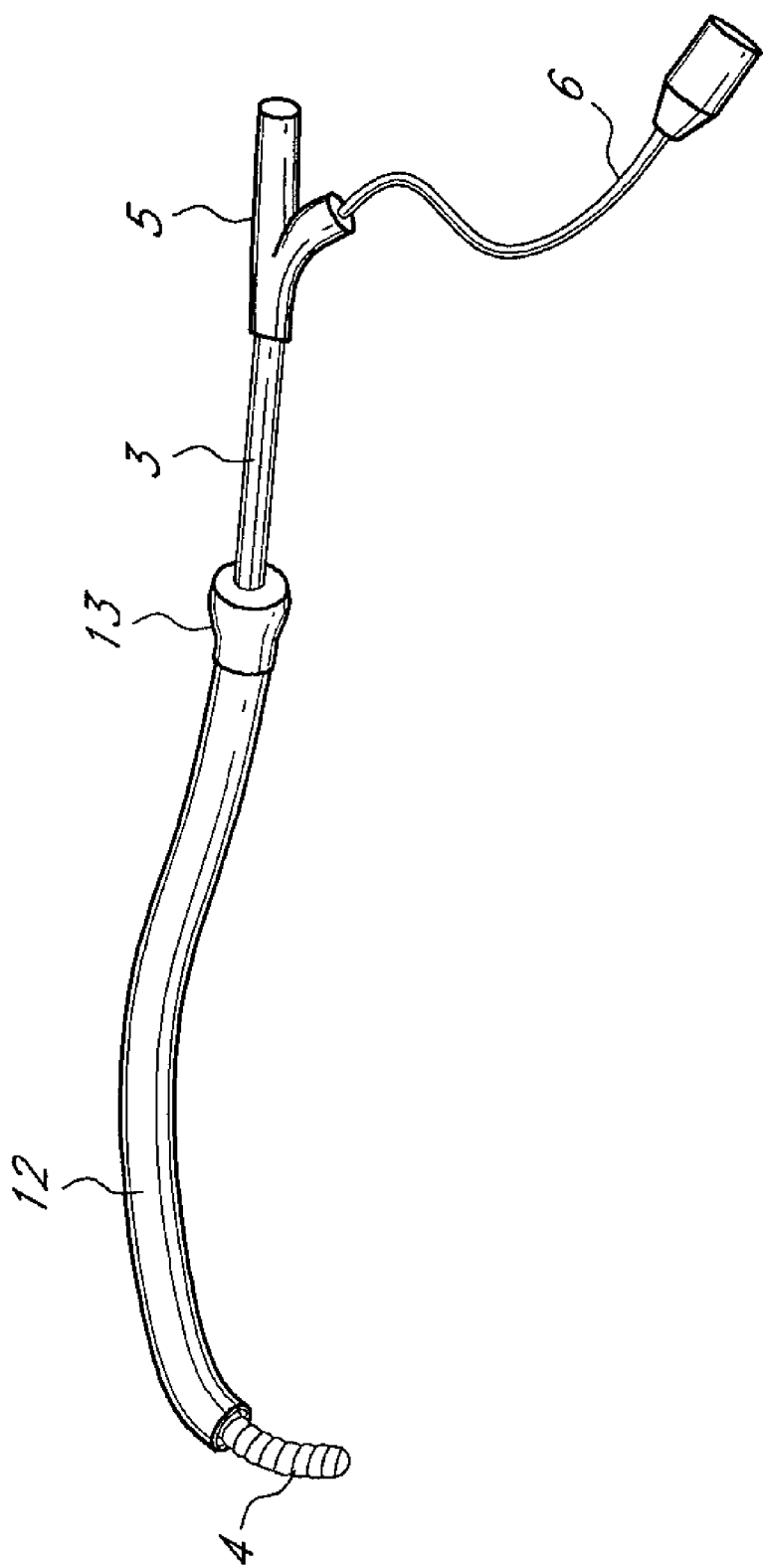
FIG. 2 illustrates an exemplary embodiment of a catheter sheath in a partially retracted position usable with the resistive element system of FIG. 1.

FIG. 2 illustrates another embodiment of the resistive element system. As shown, the catheter includes an outer retractable sheath 12. The sheath 12 is advantageously used to protect the device during placement, facilitate introduction of the device, and/or adjust the exposed axial length of the resistive element for a user-selected and variable treatment length. For example, the sheath 12 may be used (e.g., pulled back (proximally) or pushed forward (distally)) to adjust the length of the heated region of the catheter that is exposed to a wall of the hollow anatomical structure.

Figure 3:
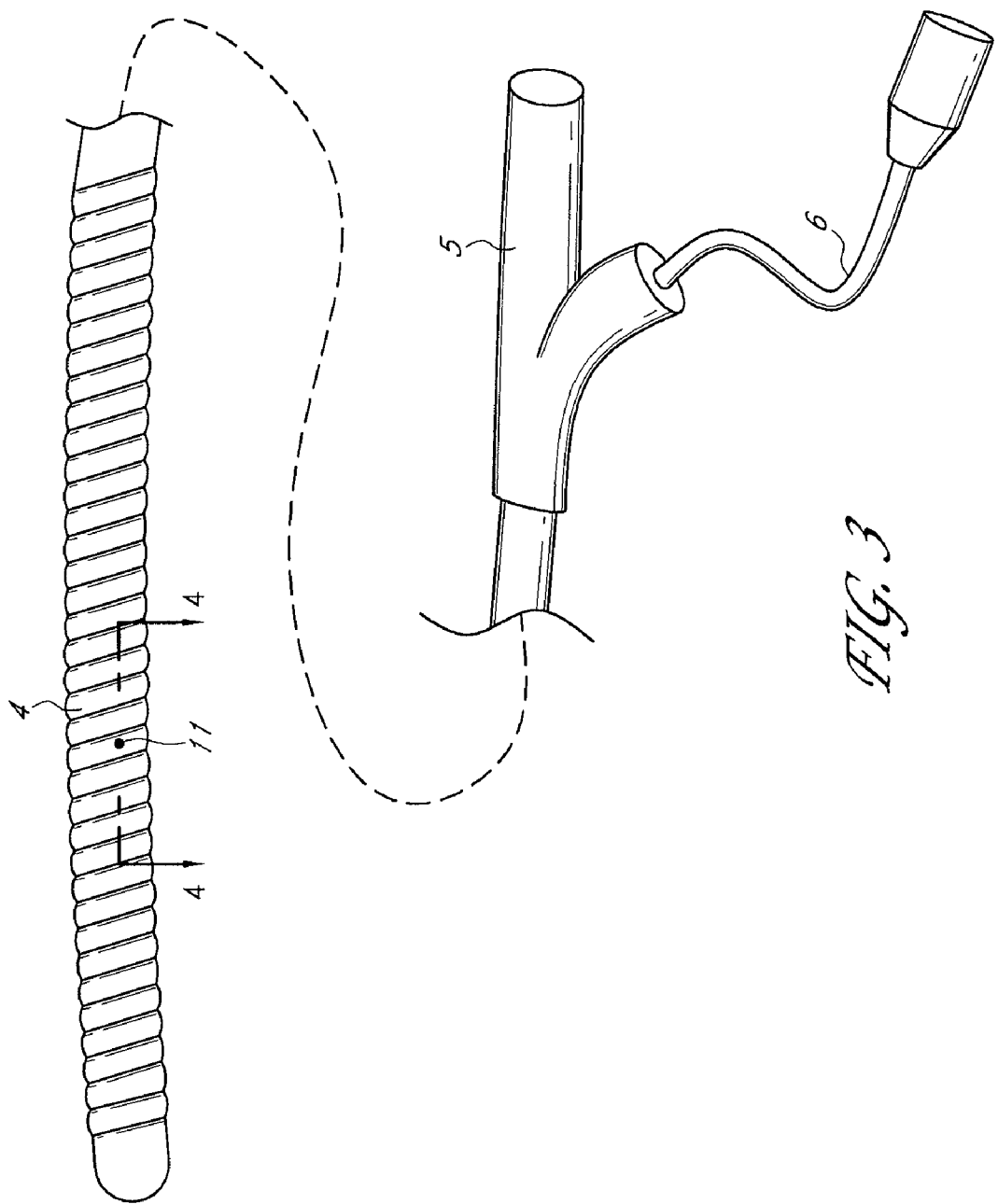
FIG. 3 illustrates a closer view of an exemplary embodiment of a catheter usable with the resistive element system of FIG. 1.
Figure 4:
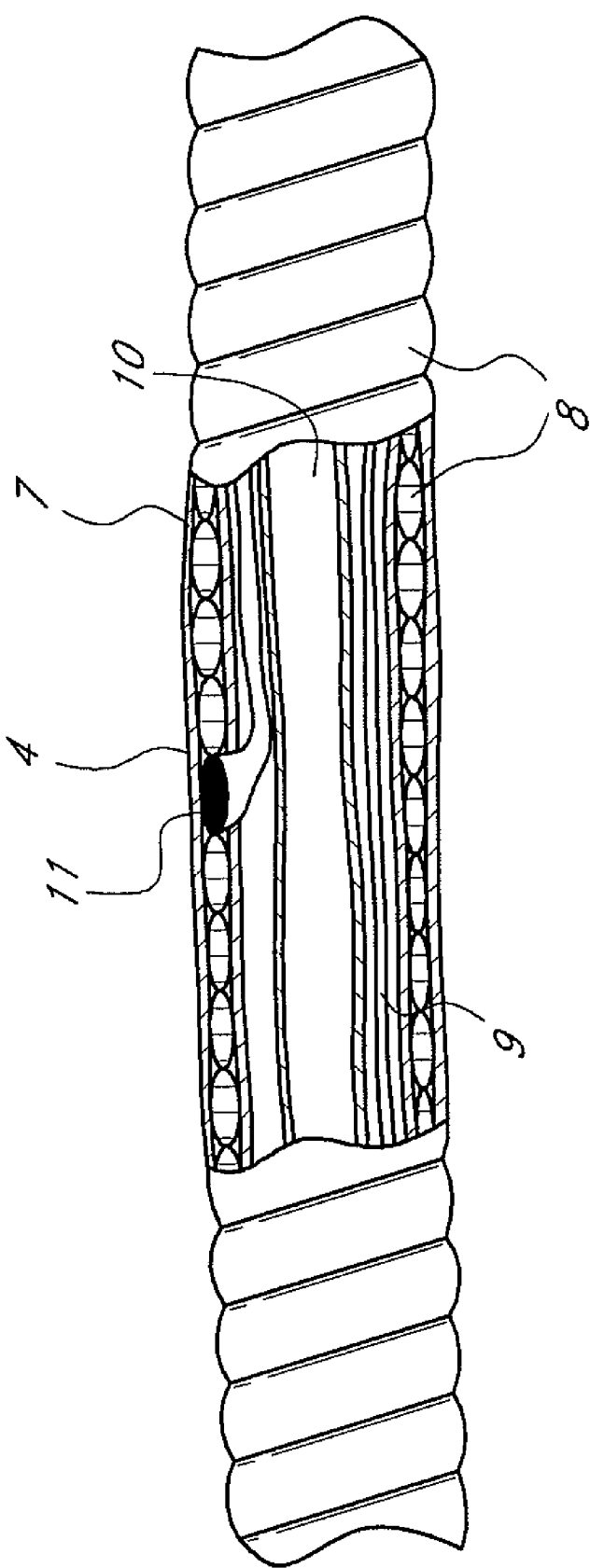
FIG. 4 illustrates a cross-sectional side view of a working end of the catheter of FIG. 3.

FIG. 3 illustrates the catheter 1 with a section A-A, which is further depicted in FIG. 4. In particular, FIG. 4 illustrates a detailed cross sectional portion of the resistive element and internal components of the catheter 1. As will be appreciated, the distance between the illustrated adjacent coils 8 may be of consistent or varied spacing.

The distal section 4 in FIG. 4 shows the resistive element 8 covered by a sleeve 7. In one embodiment, the sleeve 7 is a thin-walled tube from 0.00025" to 0.003" thick. In other embodiments, sleeve may have a wall thickness of less than 0.00025" or of more than 0.003". In one embodiment, the sleeve 7 comprises PET (polyethylene terephthalate). In other embodiments, the sleeve 7 may comprise TEFLON®, polyimide or other thin walled sleeve material which remains substantially stable for the desired temperature range. The material selection process of sleeve 7 may be determined by polymers with nonconductive or electrically insulative properties.

FIG. 4 also shows an internal lumen 10 of the catheter, which communicates through an open lumen from the distal tip to the proximal handle. In one embodiment, the lumen 10 is used for delivery of fluids, such as for example, saline, a venoconstrictor, sclerosant, high-impedance fluid, physiologic tissue adhesive, hydrogel, or the like. In addition, upon completion of treatment, a hydrogel may be exuded from the distal catheter end allowing for complete vessel occlusion. For example, the hydrogel may be biocompatible or bioresorbable. In other embodiments, the hydrogel may be displaced by the constriction of the hollow anatomical structure resulting from the thermal injury response which results in substantially complete occlusion. In those sections of the hollow anatomical structure in which the material has not completely compressed, it can be resorbed by the body naturally. In yet other embodiments, the lumen 10 may also accommodate a guide wire for catheter placement.

In one embodiment, the resistive element 8 is made of resistive wire that generates heat when the energy source is connected and applied to the catheter. As shown in FIG. 4, the resistive wire comprises a round cross-section. In other embodiments, the resistive wire may alternatively be rectangular, ovular, or another geometrical cross-section. Preferably, the relative resistance or impedance of the resistive element 8 is designed to correlate to the energy source. For example, the resistance of resistive element 8 may be determined by a wire gage that relates to the catheter diameter, the energy required, and the energy source requirements. The wire may comprise a wide variety of conductive materials, such as, for example, nickel chromium, copper, stainless steel, NITINOL®, ALUMEL®, and the like.

The resistive element 8 illustrated in FIG. 4 is a closed wind coil (i.e., with substantially no inter-coil spacing). In one embodiment, an electrical connection, such as soldering at the proximal end and/or the distal end of the coil, couples the resistive element 8 to a signal wire 9. As shown in FIG. 4, the signal wire 9 is a distal return signal wire. For example, the signal wire 9 may run the internal length of the catheter 1 to a connector cable 6. In one embodiment, the signal wire 9 extends from the proximal end of the coil. In such an embodiment, the signal wire 9 is a larger gage copper wire (e.g., 28 to 34 gage) in order to reduce possible heating within the main body of the catheter 1.

In one embodiment, the resistive element 8 comprises a constant, closed-pitch coil. Alternatively, the resistive element may have a varying pitch and/or a varying inter-coil spacing. For example, a varying coil pitch and/or spacing may be advantageously used to vary the heat output over the axial length of the heating element. An axially (and/or radially) varying heat output from the resistive element is useful in providing a substantially uniform tissue and/or device temperature during treatment. For example, such a variation in coil pitch may be advantageous in situations involving fluid flow within the hollow anatomical structure. In such cases, the fluid tends to absorb heat output from the proximal portion of the resistive element to a greater degree than heat output from the distal portion. This can result in a reduction of the heat actually applied to the wall of the hollow anatomical structure adjacent to the proximal portion of the resistive element relative to the central and distal sections. As the fluid flows past the proximal section of the heating element, the fluid itself will be heated. The heated fluid then flows across the middle and distal sections of the resistive element 8, thereby increasing the temperature of treatment for these sections. One embodiment, intended to counteract this effect, comprises a close-pitch wind of the heating element in the proximal portion (implying a higher heat output in the proximal portion) while the middle and distal sections may have a comparatively more open-pitch wind (i.e., the inter-coil spacing increases in the distal direction). This configuration decreases the heat output along portions of the coil in order to compensate for the added heat from the proximal adjacent sections. That is, the variable coil pitch may be used to correct for higher temperatures of the middle sections of the resistive element in comparison with lower temperatures of the end sections of the resistive element. A thermally-insulating material (such a natural rubber, silicone, or an elastomer) may be used to shield the internal lumen from heating, or to selectively reduce external heat transfer from the resistive element.

In another embodiment, portions of the resistive element having a close-pitch wind are used to heat larger portions of an anatomical structure (e.g., portions having a larger diameter) while portions of the resistive element having an increased coil spacing are used to heat smaller portions of the anatomical structure (e.g., portions having a smaller diameter).

In other embodiments, the coil wind comprises more than one radially displaced layer. For example, as shown in FIG. 5, the successive layers 14 and 15 of winds may be counter-wound to overlap and can also have a variable pitch over the axial length of the shaft. This configuration may be used to provide a greater heating density, or to provide more uniform heating if the coil winds are spaced to increase the length of heating segment with a limited length of coil wire.

In one embodiment, the resistive element 8 comprises a bifilar wire coil, which is advantageous in processing as it can be wound as a single filament. A bifilar wire also maintains a constant distance between the two embedded wires, which can help to maintain accurate overall spacing in order to provide uniform heat distribution. In some embodiments, the wind of the bifilar wire coil may comprise a variable pitch, as discussed previously. The bifilar wire coil may also combine wire connections (i.e., connections between the multiple wires in the wire coil) at one end of the catheter, preferably the proximal end. For example, the distal end may comprise an electrical connection between the two wire ends in order to create a continuous loop. In alternative embodiments, the bifilar wire can comprise more than 2 wires.

FIG. 6 shows the bifilar wire 16 coupled through solder joints 17 to signal wires 18 and 19. In one embodiment, the joints 17 are spot welded or bonded with a conductive epoxy. In addition, the signal wires 18 and 19 may extend internally through the catheter shaft to the connector 6 located at the proximal end (e.g. see FIG. 1). As previously discussed, FIG. 6 shows one example of a variable wind configuration.

In other embodiments of the invention, energy is applied separately to each wire of the bifilar wire coil. For example, applying energy separately to each wire may be used to vary and control the power and heat transferred from the device to the vessel. In one embodiment, a single coil is used for smaller hollow anatomical structures, while both coils are used with larger hollow anatomical structures.

FIG. 2 shows a single sensor as part of the resistive element. In other embodiments, multiple sensors are placed along the axial resistive element length. For example, the energy source may advantageously monitor the individual sensors and use the multiple inputs for temperature feedback. In another embodiment, the controller may monitor for high temperature or low temperature signals. For example, an algorithmic process may be used to control the current applied to the various wire coils, thus maintaining a substantially axially-uniform temperature and/or heat output.

Figure 7:
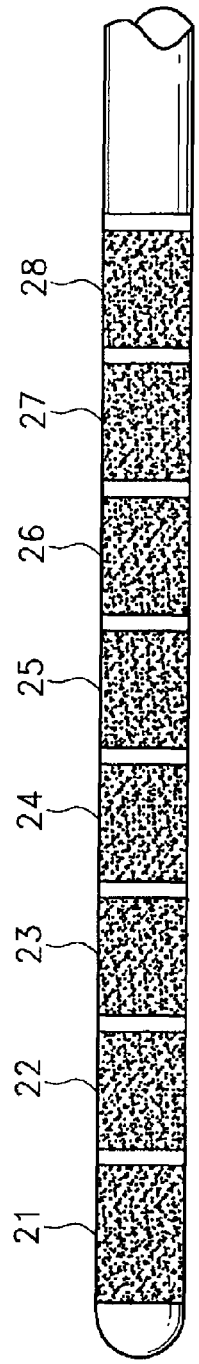
FIG. 7 illustrates a side view of yet another embodiment of the working end of the catheter of FIG. 3.

In another embodiment, the resistive element 8 comprises multiple coils, which are sequentially placed axially on the catheter shaft represented by the resistive elements 21 through 28, as shown in FIG. 7. For example, each resistive element may be individually temperature controlled and/or may comprise a temperature sensor.

Alternatively the sequential resistive elements may be used in a power control mode that relies on manual energy control.

Alternatively, in one embodiment of the invention having multiple resistive elements, a temperature sensor is located on the most distal resistive element. For example, the most distal resistive element may be used for the initial treatment and the successive coil electrodes may use the same and/or a predetermined energy-time profile.

Figure 7A:
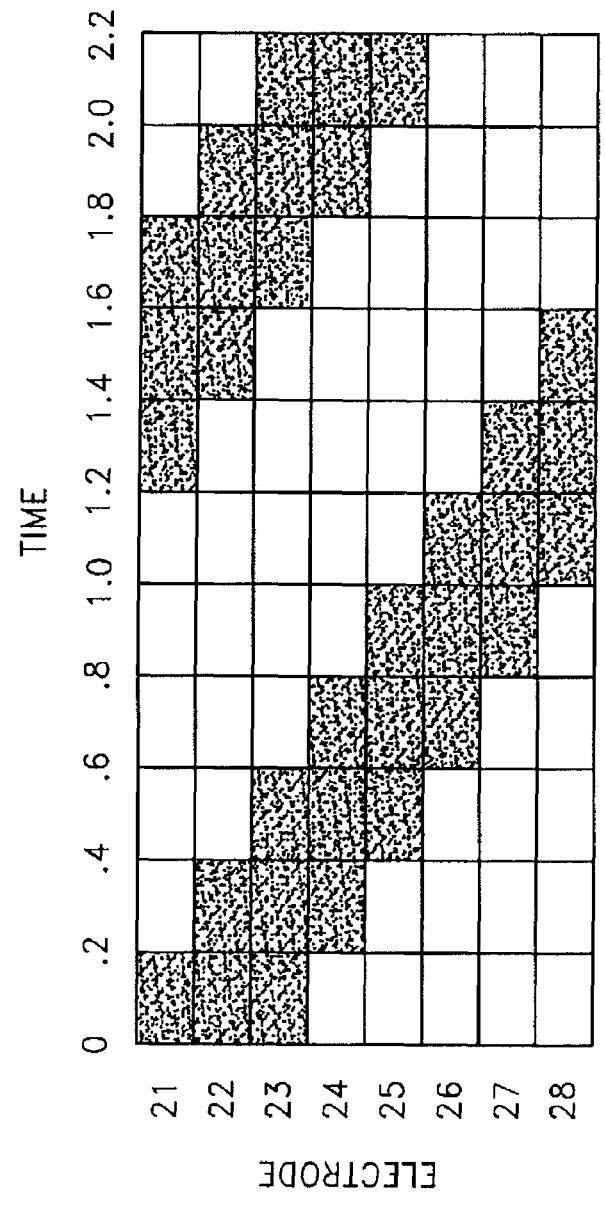
FIG. 7A is a table depicting an exemplary treatment cycle usable with the catheter of FIG. 7.

In one embodiment, a method of use of the resistive element system includes multiplexing through each of the resistive elements 21-28 shown in FIG. 7A. The term "multiplex" as used herein is a broad term and is used in its ordinary sense and includes without limitation the energizing, or heating, of at least one resistive element for a specific dwell time and cascading, or moving, to another resistive element until the end resistive element is reached or until a cycle is completed. The cycle is then repeated until the complete treatment time is reached.

FIG. 7A shows an example using the resistive element configuration shown in FIG. 7. In one embodiment, the resistive elements 21 through 28 are sequentially energized for a dwell time of approximately 0.2 seconds. In the example shown, three resistive elements are powered at a time. The table has shaded blocks of time, which represent the time that energy is being delivered to the specified resistive elements. Since three resistive elements are on at one time and the dwell time is 0.2 seconds, each resistive element is on for a total of 0.6 seconds during one cycle. In the table, for time 0 to time 0.2 seconds, resistive elements 21, 22 and 23 are energized. For time 0.2 seconds to 0.4 seconds resistive elements 22, 23 and 24 are energized. This process repeats by stepping through the resistive element set. For the 8 resistive elements shown, one complete cycle takes 1.6 seconds. In one embodiment, to avoid overcooling of a particular resistive element, the cycle time is of a short duration and/or the total number of resistive elements is limited. That is, in one embodiment, a resistive element may be re-energized before substantial cooling takes place. In addition, in one embodiment, to increase the treatment zone, the catheter may comprise multiple treatment zones, such as for example, groups of eight resistive elements, as is shown in FIG. 7. Each group of eight resistive elements may treat the wall of the hollow anatomical structure before energy is applied to the next group of resistive elements. Alternative modes of multiplexing may also be employed. For example, the number of adjacent resistive elements simultaneously energized may vary. Also, the entire cycle may re-start at the first end energized, or the last end energized. Another mode of multiplexing may be accomplished through a sensing of the tissue impedance. Once a certain level is achieved, the next set of resistive elements is then energized.

Alternatively, at least one of the eight resistive elements is energized to treat the hollow anatomical structure until treatment is complete. Then, the next resistive element(s) apply a similar treatment time, and so on moving along the treatment zone. For the eight resistive elements illustrated in FIG. 7, the treatment may be for one cycle. For example, resistive element 21 may treat the hollow anatomical structure for approximately 20 seconds. Once resistive element 21 has completed treatment, resistive element 22 repeats the same treatment time and energy settings. Such a process may continue for resistive elements 23 through 28.

In other embodiments of the invention, alternate treatment cycles may be used. For example, resistive elements 21 and 22 may concurrently treat the hollow anatomical structure for approximately 20 seconds. Then resistive elements 23 and 24 apply a similar treatment, and so forth through resistive elements 27 and 28 to complete the cycle.

Figure 7B:
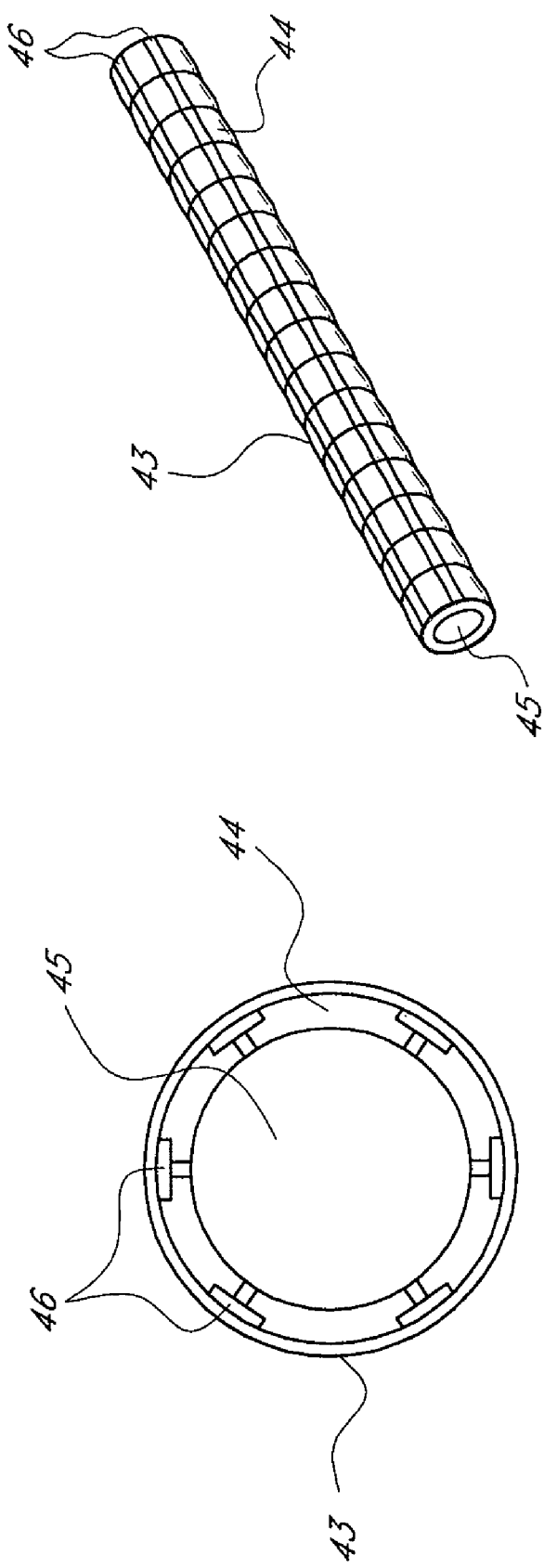
FIG. 7B illustrates two views of an embodiment of a catheter incorporating external fluid grooves and an external coil electrode.

FIG. 7B illustrates another embodiment of an electrically resistive heating element having an open pitch wind, but omitting an outer sleeve 7. FIG. 7B shows the coil spacing greatly exaggerated in order to see the tube detail 44. In one embodiment, the inter-coil spacing is selected to create a path for fluids. For example, the inner lumen 45 (which is shown as a single lumen, but may include multiple lumens) of the catheter may deliver fluid to the vessel by the additional pathways 46 which are external surface features and radial holes (intermittently spaced along the grooves) in the tube wall. The fluid may be a saline, a venoconstrictor, or the like. In one embodiment of a method of using the device of FIG. 7B, the device is placed in the hollow anatomical structure. The hollow anatomical structure is then treated with the venoconstrictor via the catheter lumen 45 and 46. Then the hollow anatomical structure is treated by heating the constricted wall of the hollow anatomical structure.

Figure 7C:
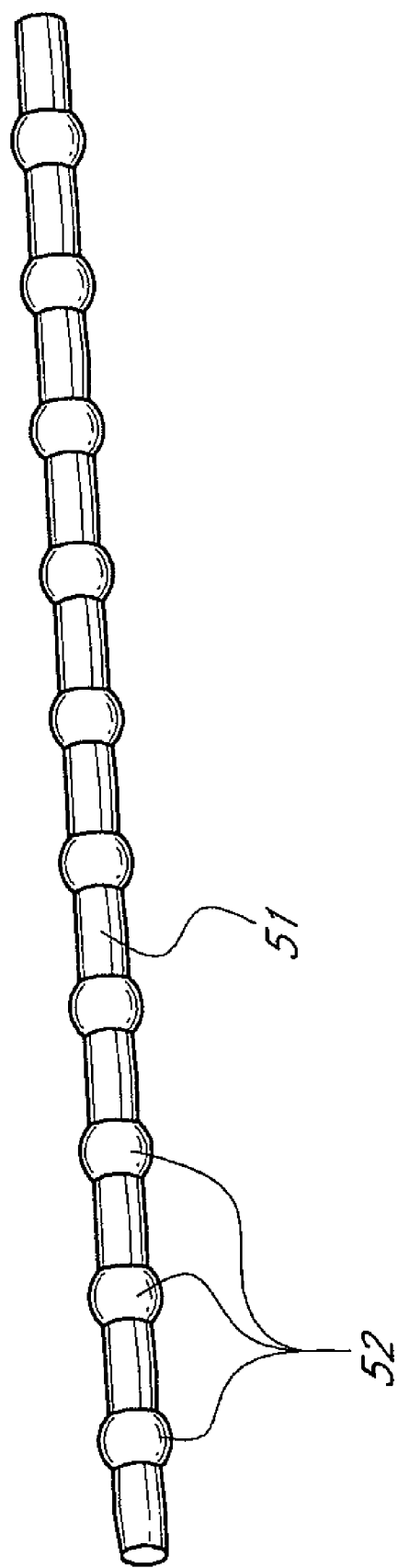
FIG. 7C illustrates an embodiment of a resistive element system having multiple protruding resistive elements.

FIG. 7C illustrates an embodiment of a resistive heating element comprising multiple resistive elements with separate and distinct protruding resistive elements made of resistive materials, such as, for example, KANTHANAL®, NICHROME®, CHROMEL®, ALUMEL®, KOVAR®, Alloy 52, TITANIUM, ZIRCONIUM, combinations of the same or the like. In one embodiment, a series of resistive elements are spaced axially along the catheter shaft; each of these resistive elements comprises a doubly-truncated-spherical body 52. In one embodiment, each resistive element may be attached to a signal wire by solder, spot weld, or other method. For example, the signal wire may run internal to the catheter tube and attach to the cable and connector 6.

Figure 7D:
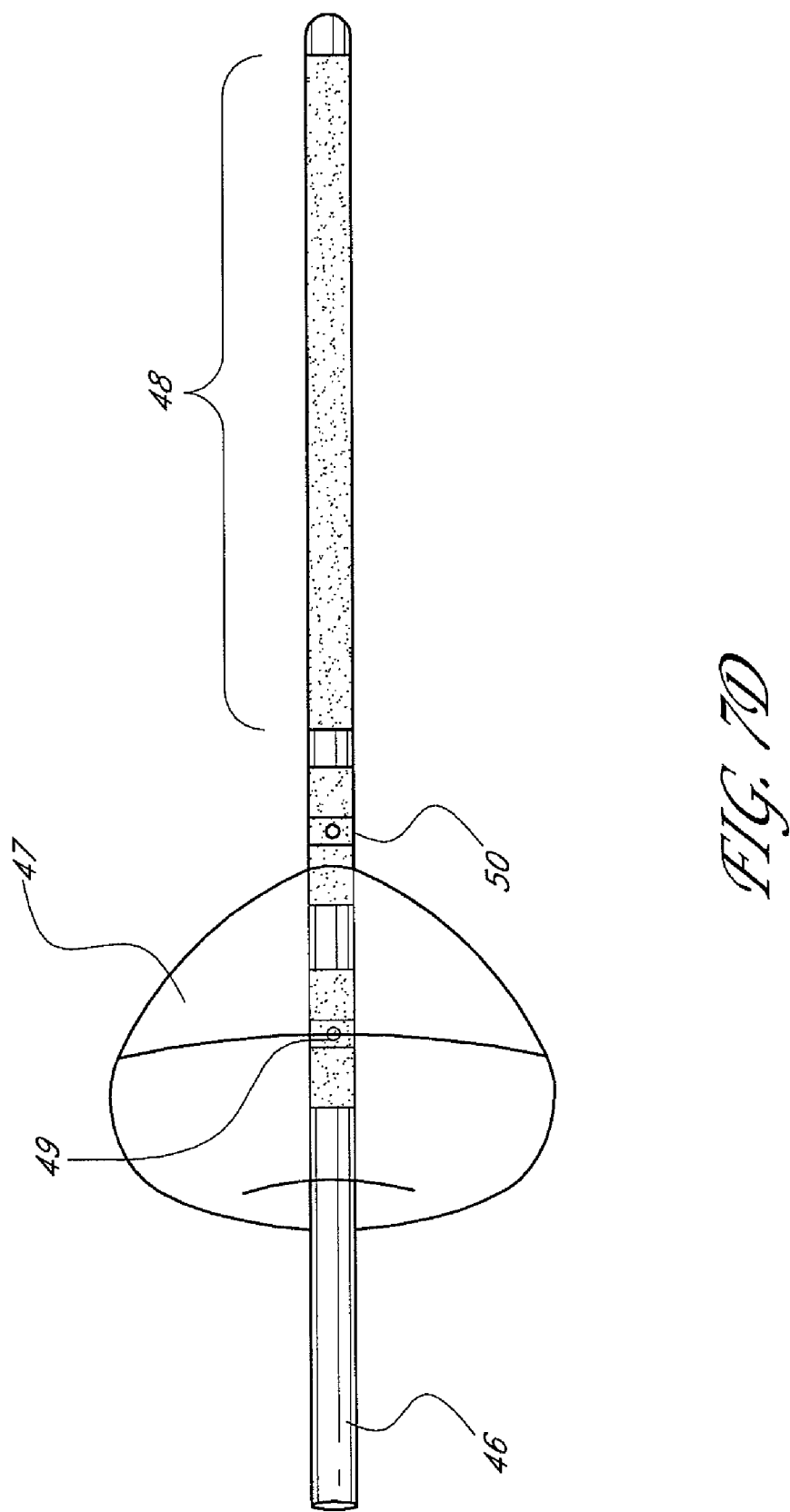
FIG. 7D illustrates a side view of a resistive element system including an expandable balloon and a set of fluid ports, according to one embodiment of the invention.

FIG. 7D is another embodiment of the working portion of the catheter. The device shown has the addition of a balloon 47, expanded by ports 49. As shown, the balloon 47 is located proximate to the resistive element. The balloon 47 may be used to occlude or substantially occlude a hollow anatomical structure. Additional fluid ports 50 proximal to the resistive element 48 are for fluid placement within the hollow anatomical structure.

In one embodiment, the catheter is placed in the hollow anatomical structure, and then the balloon 47 is inflated through the ports 49. Once the balloon is inflated, the fluid ports 50 clear the hollow anatomical structure of native fluid, such as blood, distal to the balloon 47, by injecting a displacing fluid, such as, for example, saline. In one embodiment, the displacing fluid is followed by another injection of a venoconstrictor, which reduces the hollow anatomical structure lumen size prior to treatment. By temporary reduction of the hollow anatomical structures size, the treatment time used for the resistive element 48 is reduced, thereby resulting in a more effective and safe treatment.

Figure 8:
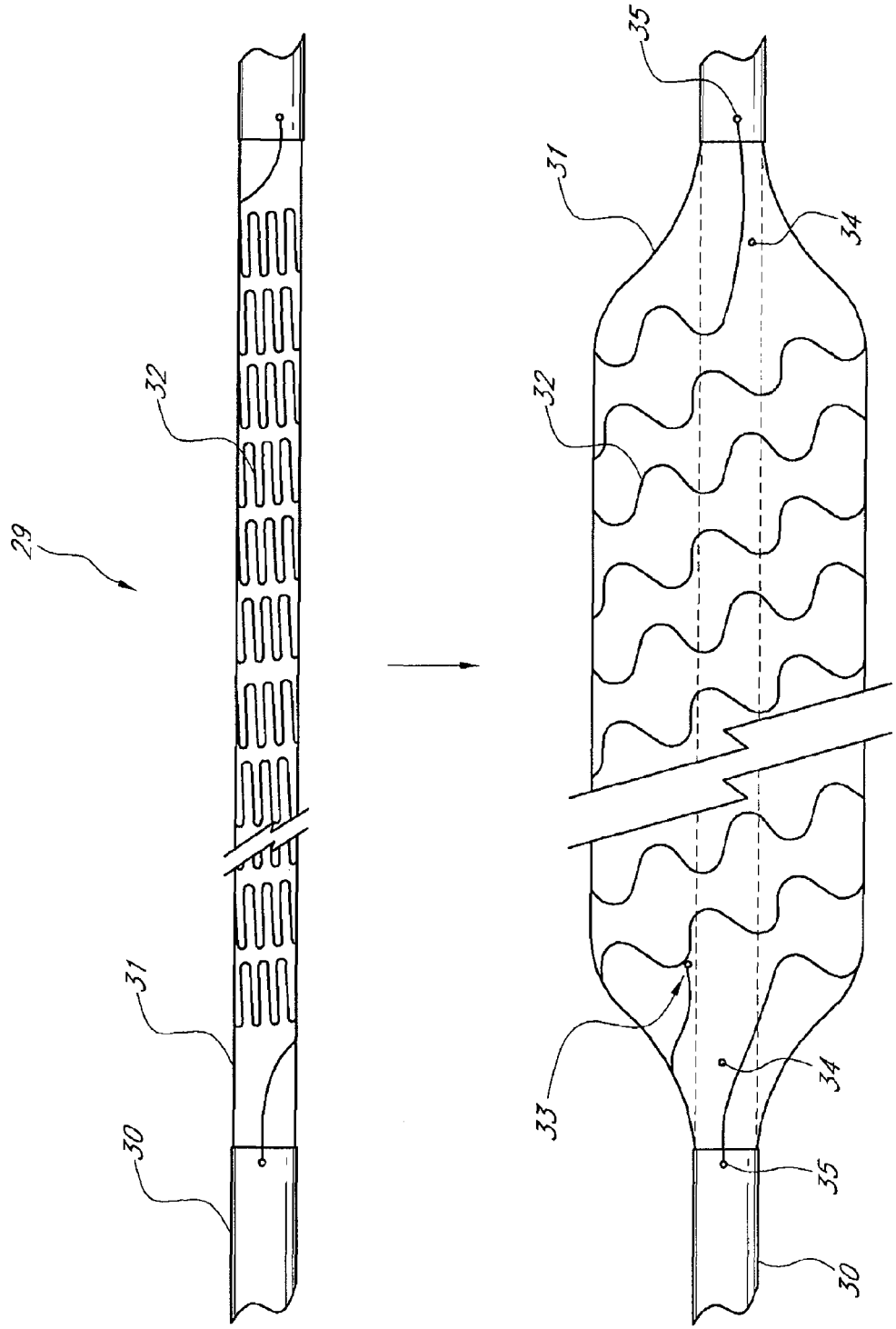
FIG. 8 illustrates another embodiment of an expandable device having an expandable electrode.

Expandable Resistive Element Devices:

Serpentine:

Another embodiment is shown in FIG. 8, which incorporates an expandable resistive element 32 on a balloon 31. In one embodiment, the balloon 31 is made of a biocompatible material such as, but not limited to silicone, PET, urethane, latex, C-FLEX®, combinations of the same or the like. The balloon 31 is attached to the catheter shaft 30 at the working end of the catheter. Both ends of the balloon are sealed on the shaft and are fluid tight. The catheter shaft section within the balloon contains fluid ports (not shown). The ports are connected to internal open lumen(s) which run internally to the shaft to the proximal end. The lumen(s) at the proximal end at the handle 5 are connected to luer components for external fluid connections. These are used to expand and collapse the balloon.

The resistive element 32 is a serpentine component, which is placed circumferentially around the exterior of the balloon 31 and catheter shaft. In one embodiment, the serpentine component expands circumferentially as the silicone balloon expands. In one embodiment, the serpentine component 32 is made of NITINOL®. For example, the shape memory aspect of NITINOL® may be advantageously utilized to help the component remember its expanded or collapsed position. In other embodiments, other nickel based spring alloys, other spring alloys, 17-7 stainless steel, Carpenter 455 type stainless steel, beryllium copper, or other similar materials may also be used.

In an alternate embodiment, the serpentine component 32, is located within the wall of the balloon material or between two layers of the silicone balloon material. This embodiment results in the serpentine resistive element being more integral to the assembly.

A temperature sensor 33 is attached to the serpentine component for temperature control during application of the energy. In FIG. 8 the sensor is attached near the proximal end of the serpentine, but may be attached at any point axially. In one embodiment, the attachment of the sensor is accomplished by soldering, bonding or essentially tying it onto the section of the serpentine wire. The ends of the serpentine component 35 are attached to signal wires, which run through the catheter internal open lumen and are connected to the connector cable 6. These signal wires may be attached by solder (or previously discussed methods) to the serpentine component.

This embodiment of FIG. 8 places the resistive element in apposition to the wall of the hollow anatomical structure prior to treatment by use of the expanding balloon 31. Thus, one device may be adjusted to fit multiple sizes of hollow anatomical structures. The balloon 31 and serpentine component may also collapse during the last portion of the treatment or as the treatment is completed. The intent of collapsing the device during the last portion of treatment is to maintain apposition with the walls of the hollow anatomical structure while allowing the tissue to shrink and/or constrict in order to occlude.

For improved viewing of the balloon during expansion, a contrast medium may be used for fluoroscopy or an ultrasonic contrast. For example, micro bubbles may be employed as part of the balloon fluid for expansion. This can be applicable to any expandable resistive element using a fluid filled balloon.

In one embodiment, the balloon is capable of displacing a substance, such as blood, from a treatment area. In another embodiment, the balloon is further capable of directing heat toward the wall of an anatomical structure by bringing at least a portion of the resistive element in proximity with, or in contact with, the wall. In yet other embodiments, the balloon is configured to collapse in response to the collapsing or narrowing of the anatomical structure and/or is configured to collapse manually.

In one embodiment, an indicator in the handle of the resistive element system shows the state of inflation of the balloon. For example, the indicator may comprise a substance or display that moves axially to show deflation of a balloon. For instance, the indicator may be coupled to the expandable member (e.g., the balloon), such that expansion of the expandable member causes corresponding changes (e.g., movement) of the indicator. In other embodiments, the outflowing saline is employed in a pressure or level-gauge like configuration (e.g., a thermometer-like configuration) to indicate the state of inflation of the balloon.

Figure 9:
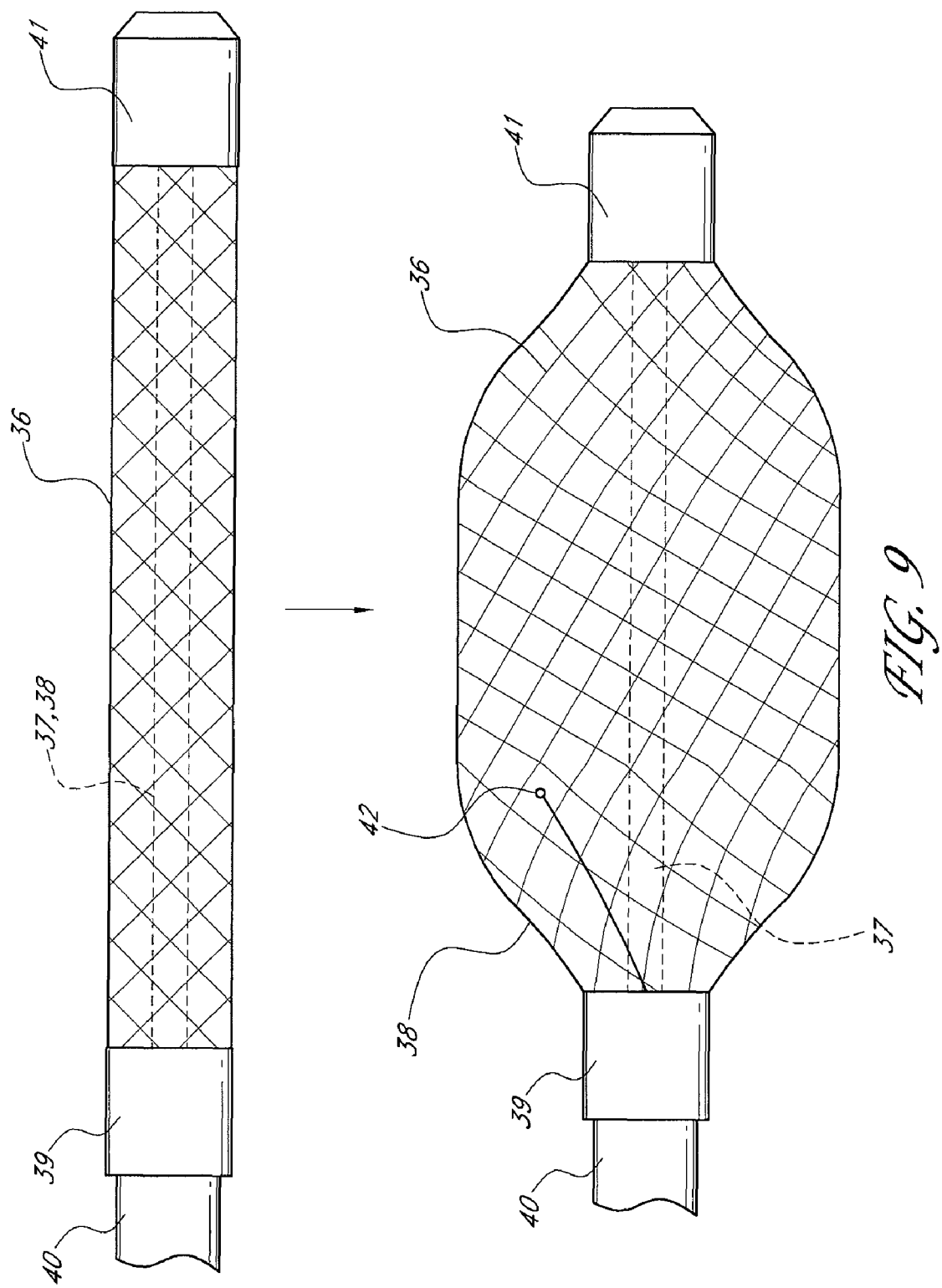
FIG. 9 illustrates yet another embodiment of an expandable device having an expandable braid electrode.

Expandable Braid:

FIG. 9 illustrates another embodiment of an expandable resistive heating element. This embodiment utilizes a metal braid wire 36 as the working resistive element. In one embodiment, the wire is round and made of NITINOL®. However, in other embodiments, the braid wire may be flat wire and/or comprise another spring-type or shape memory material as discussed above. For the device, the elastic characteristics of NITINOL® are beneficial to the method of expanding and collapsing the device. In one embodiment, the braid is heat set in the nearly fully expanded position. In other embodiments, the balloon is used to expand the braid.

In one embodiment, the braid wire is sleeved in polyimide to isolate the wires from each other where they overlap. In other embodiments, other materials may be used, such as for example, TEFLON®, urethane, and the like. The braid component may be created using standard braiding technology. Alternatively, a single wire may be woven into the braid component. The method is relevant for the overall resistance or impedance of the device for the energy source.

The proximal and distal ends of the braid 36 component are captured in a two-part crimp sleeve, 39 and 41, in order to anchor the ends to the catheter tube, 40 and 37. The braid 36 in this embodiment is expanded by the use of the catheter stylet 37, which runs the internal axial length of the catheter, from the distal tip 41 to the proximal handle 5. The proximal end of the stylet passes through a Touhy Borst type fitting on the catheter handle 5 and in turn is a handle for stylet manipulation. In this case, pushing the stylet 37 distally collapses the braid (illustrated in the upper figure of FIG. 9), while pulling the stylet 37 expands the braid (illustrated in the lower figure of FIG. 9).

In the embodiment of the invention illustrated in FIG. 9, a balloon 38 is placed internal to the braid 36 such that the ends are distal to the crimp section 39 and proximal to the crimp 41. As previously discussed, the balloon 38 is silicone, but it can be of other materials previously identified. This balloon then uses internal lumen and side port (not shown) of the catheter stylet 37 for inflation and deflation.

It should be noted that the typical silicone extrusion may expand axially and radially when inflated. This causes the balloon to become "S" shaped for a set axial length of tubing, thus causing the braid to have non-uniform tissue apposition with the hollow anatomical structure. To compensate for this issue, the extrusion 38 may be pre stretched axially just prior to anchoring on the catheter tubing to the stylet component 37. The stretched tube may then expand radially with little to no axial expansion, depending on the amount of pre-stretch done. The balloon may be used to occlude the vessel to impair blood flow and to remove blood from the braid portion of the catheter. This creates a static fluid volume and makes the heat treatment more efficient. Also, the balloon promotes braid apposition with the hollow anatomical structure. In other embodiments, the balloon is at least partially expanded and contracted through expansion and compression of the ends 51, 54.

In one embodiment, a temperature sensor 42 is attached to the braid wire along its axial length. The sensor 42 may be used for temperature control during the application of energy for the controller. Although the sensor 42 is shown attached near the proximal end of the braid wire, the sensor 42 may be located along other portions of the braid wire. In addition, more than one sensor may be used.

In another embodiment, the balloon is a separate device from the braid device. For example, the balloon device may fit within the lumen of the braid device, and the tips of both devices may connect and anchor to one another. For example, the anchor mechanism may include a set of male and female threads appropriately sized. Alternatively the device tips may be anchored together by use of axially aligned holes in both tips, through which a wire is placed and tied off. Alternatively, the tips may be designed with a spring ball detent to anchor the tips together. Alternatively, strong magnets of opposite polarity may be used to locate the tips and hold them together.

Figure 10:
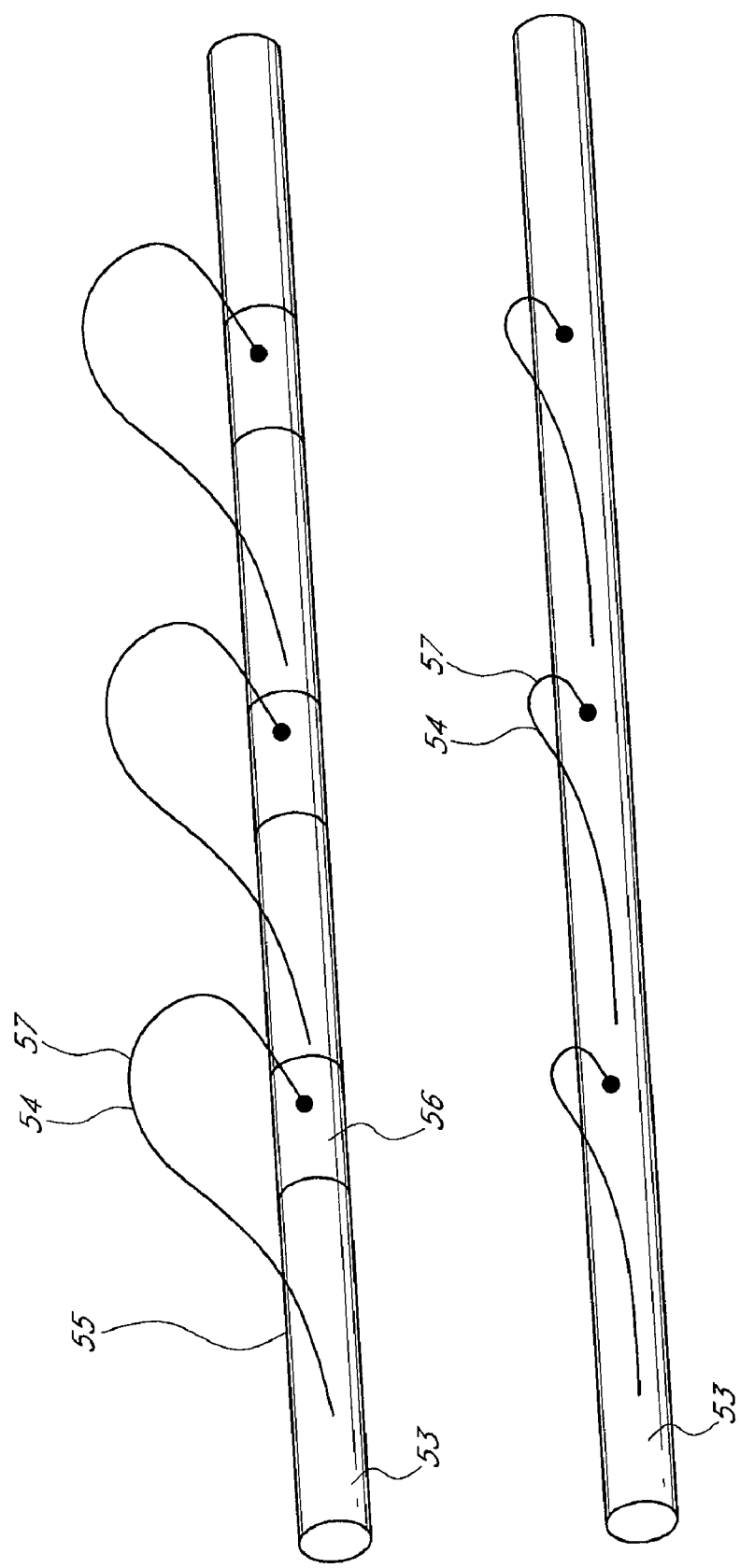
FIG. 10 illustrates another embodiment of a working portion of the catheter body with individually expandable loops.

Expandable Loop:

Another embodiment, shown in FIG. 10, utilizes at least one expandable loop, which emanates from the side of the main catheter body. One end of the loop 55 is anchored to the catheter shaft 53. The other end of the loop passes through an opening 56 in the sidewall of the catheter tube 53 and runs through the catheter lumen to the handle 5 at the proximal end. This end of the loop acts like a stylet, in order to manipulate the loop shape and size. In one embodiment, the wire coils around the main catheter body with spaced attachment points (such as by entering into and exiting from segments of a lumen within the main catheter body) such that by advancing the wire the coils extend beyond the main catheter body in the fashion of circular coils tending toward a right angle to the axis of the main catheter body. The wire is typically circular in cross section. In one embodiment, the loop is pre-shaped in order to extend outward toward the walls of the hollow anatomical structure and eventually into contact with them. Alternatively the wire section that forms the actual exposed loop portion 54 may be a flat wire, rectangular, ovular, or other geometrical cross section. In one embodiment, rotating the stylet handle end of the loop manipulates, or twists, the loop toward or away from the catheter shaft.

The loop 54 may comprise a resistive element similar to the element 4 of FIG. 1. For example the loop 54 may comprise a resistive element coil 57 wrapped around it. In addition, each loop may have a temperature sensor on the resistive element 57 for use in temperature controlled energy delivery. In other embodiments, each resistive element is covered with a sleeve. For example, the sleeve material may comprise PET, TEFLON®, polyimide, or other material.

Wavy Expandable Length:

Another embodiment is shown in FIG. 10A and utilizes at least one expandable formed set of bends. A main spline 73 shown in FIG. 10C makes the backbone and is made of NITINOL®. In other embodiments, the spline 73 is made of other nickel-based spring alloys, 17-7 stainless-steel, Carpenter 455 type stainless-steel, or beryllium copper, or other similar materials. An embodiment illustrating details of the spline 73 is shown in FIG. 10C. The illustrated spline 75 is wound with a resistive wire 76 as previously discussed in detail with respect to FIG. 4. The device illustrated in FIG. 10A may also include a temperature sensor. Because the illustrated spline 73 slides into the tube 70, it has an outer sleeve 77 made of TEFLON® for reduced frictional force.

In one embodiment, the spline 73 is straightened by withdrawing it proximally into the tube 70. For example, the tube 70 may comprise an inner liner 72, which extends out of the tube end and is formed into an outer lip 71. In addition, FIG. 10A-10C show the spline 73 as 2-dimensional. However, a skilled artisan will recognize from the disclosure herein that the spline 73 may also comprise various 3-dimensional shapes, such as for example, a helical wind. This shape may be used to improve contact of the heating element to the wall of the hollow anatomical structure during the treatment cycle.

Figure 11:
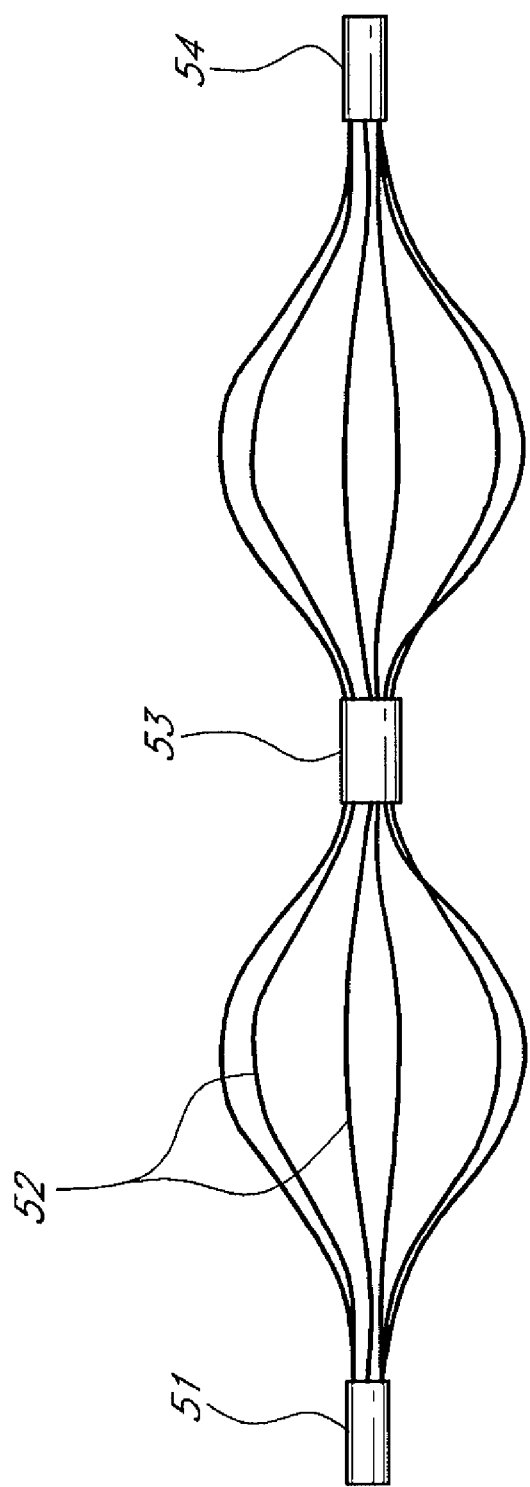
FIG. 11 illustrates an exemplary embodiment of an expandable set of spline electrodes capable of conforming and contacting a vein wall.

Expandable Floating Ribbon:

FIG. 11 illustrates another embodiment using at least one expandable resistive element. The pre-shaped splines 52, 6 splines in this figure, act as individual resistive heating elements. The set of splines 52 are attached radially about the catheter shaft 51. The expandable resistive element set has at least one expanded section. In FIG. 11, the device shown has 2 expandable sections. The resistive element set is anchored at the mid point 53, which does not substantially expand. The tip 54 and proximal end attached to the shaft 51 also do not substantially expand.

The device is designed to collapse by use of an outer sheath, which in FIG. 11 is in a retracted position. For example, the sheath may be used to help place the device in the vessel and to help remove the device after treatment. One intent of the self-adjusting splines is to let them expand so they will be in apposition to the tissue and adjust to any axial bends or curves in the hollow anatomical structure. As the hollow anatomical structure is heated during treatment, the lumen of the structure constricts and/or shrinks and the spline set adjusts and collapses concurrently with the lumen. This same characteristic also gives the device of FIG. 11 versatility, as it is able to accommodate varying sizes of hollow anatomical structures.

Alternatively, the device comprises a stylet wire similar to the braid device of FIG. 9 in order to collapse and expand the pre-shaped splines. In this embodiment, the splines may be manually collapsed during treatment in order to follow the occlusion of the hollow anatomical structure.

Each spline 52 is made of a resistive material as previously defined. Alternately, each spline 52 may have a resistive coil wire wrapped around it, as is previously described. A temperature sensor may also be attached to at least one spline for temperature controlled energy delivery.

In one embodiment, one long expandable section makes up the resistive element set 52. To support the length during treatment, a balloon is placed inside the spline set. For example, this balloon may use an internal lumen of the catheter (not shown) for inflation and deflation. Alternatively, as described for the braid device, the balloon may be a separate device inserted into the long expandable spline set.

As discussed earlier with respect to the fixed diameter resistive element, spline resistive elements, when individually wired for power, may be used in conjunction with a multiplexing process. Such an embodiment allows for the sequential or "cascading" heating of specific resistive element subsets of the spline set. This may involve energizing at least one spline for a specific dwell time and then cascading or moving to the next adjacent spline(s) until the end spline is reached. The cycle is then repeated until the complete treatment time is reached.

Super Elastic Expanding Ribbon:

FIGS. 12A-12C illustrate a catheter with a helical coil resistive element 55. For example, the coil resistive element 55 may be manipulated from a collapsed or small diameter coil tightly wrapped around the circumference of the catheter shaft (FIG. 12A) into an expanded, large diameter coil (FIG. 12C). In one embodiment, this coil is made of a resistive type of material as discussed earlier. The expanded coil may also be in apposition with the vein wall. In one embodiment, the catheter shaft is made of two concentric tubes, 56 and 57. The proximal shaft 56 may be slightly larger in diameter to fit over the distal tube 57. The distal tube is able to rotate about the catheter tube axis relative to the proximal tube. In the illustrated embodiment, clockwise rotation expands the resistive element (as shown in FIG. 12B) and counter clockwise rotation collapses the resistive element (as shown in FIG. 12C).

FIG. 12A shows the initial collapsed position of the device, which is, for example, how the catheter may be initially placed in the hollow anatomical structure. FIG. 12B shows mid-range of the radial expanding resistive element and FIG. 12C shows final state of the device completely expanded. The coil is adjusted to eliminate the inter coil spacing by being pushed distally. The steps described are reversed in order to collapse the device for new placement or for removal.

In one embodiment, for tube 57 to rotate and move axially, it is connected to a torquable stylet wire (not shown). This stylet runs internal to the catheter shaft and is accessible at the catheter handle. In one embodiment, the handle also allows these movements and locks the stylet in position in order to hold the resistive element collapsed or expanded.

In another embodiment, the resistive element 55 is made of NITINOL®. Using the shape memory property when heated, the resistive element 55 returns to its pre-shaped expanded coil form upon heating. In this embodiment, one end of the coil 55 is tethered to the catheter, such as for example, the proximal end. The expanded coil may also "auto collapse" as the hollow anatomical structure shrinks and/or constricts during the treatment. In another embodiment, a sheath is used to retrieve the coil after treatment.

Figure 13B:
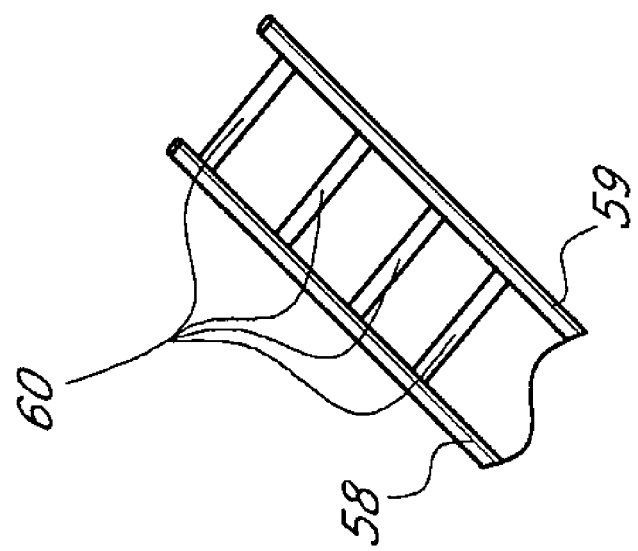
FIG. 13B illustrates an exemplary embodiment of the device of FIG. 13A having multiple strip electrodes laid flat by uncoiling the device.
Figure 13A:
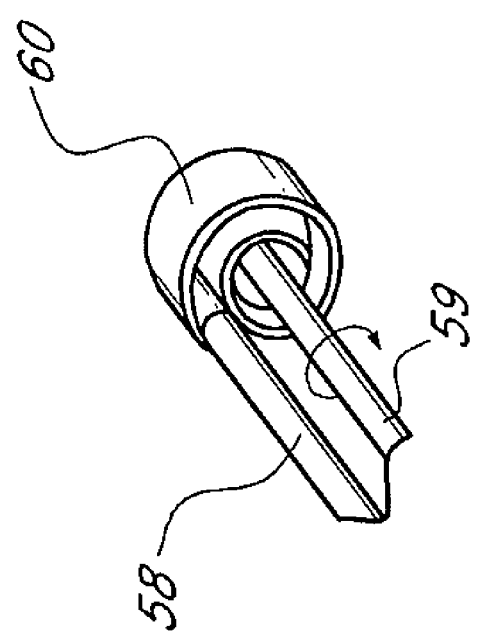
FIG. 13A illustrates an exemplary embodiment of a strip electrode coiled substantially normal to the catheter shaft axis.

FIG. 13A and FIG. 13B show another embodiment of an expandable flat strip resistive element. These are radially expanding coiled strips 60. As shown, the device has at least one strip resistive element 60. FIG. 13A shows the resistive element collapsed (i.e., coiled tightly). By rotating the stylet component 59 in the clockwise direction as shown, the resistive element 60 winds up into a collapsed coil. In the same manner, by rotating the stylet wire in the counter-clockwise direction, the coil 60 expands and adjusts to be in apposition with the wall of a hollow anatomical structure. The secondary stylet 58 is shown as a stationary component (e.g., not rotatable). In other embodiments, stylet 58 may also comprise a catheter tubing or component that attaches to the end of the resistive element.

FIG. 13B is an example of a 4-resistive element strip version of FIG. 13A and is laid out flat. In this embodiment, the resistive element strips are resistive material as previously discussed. Components 58 and 59 in this embodiment each contain at least one wire, which connects to the resistive element strips. These strips then become heated when energized. Alternatively, the strips may have resistive wire wrapped around them for coil type resistive elements As previously described, one or more temperature sensors may be attached to at least one strip for temperature-controlled energy delivery. In addition, these strip resistive elements may be used in conjunction with the multiplexing process to heat specific subsets of the group of resistive elements.

In an alternative embodiment, a resistive heating device can be configured such that the resistive heating element also acts as a resistance temperature device (RTD). Certain metals exhibit predictably varying electrical resistance properties at varying temperatures. If this relationship is known for a given resistive heating element, a temperature of the element can be determined by measuring an electrical resistance across it. Such a system may advantageously eliminate the need for additional thermocouples or other temperature sensing devices, or it may provide an independent sensing of temperature as may be used for high-temperature limitation.

In some embodiments, it is desirable to provide a heating element configured to treat a relatively short length of an HAS at a single time. Such an embodiment can be progressively moved through the HAS in a series of discrete steps from a first position to a final position in order to treat a desired length of an HAS. The process of moving a heating element through an HAS in a series of discrete steps between treatment steps is referred to herein as "indexing."

The general process can proceed by providing an elongate catheter with a short-length heating element at a distal portion thereof. The heating element and catheter can be inserted through an introducer sheath into a hollow anatomical structure such as a vein. The heating element is then advanced to a distal-most position, and power is applied. The heating element is allowed to ramp up to a desired temperature, and remains in place for a desired dwell time. Once the desired dwell time is reached, the element can be powered down, and the element can be indexed proximally to a second position, at which point at least one of the ramp up, dwell, power down, and indexing procedures can be repeated.

Figure 14:
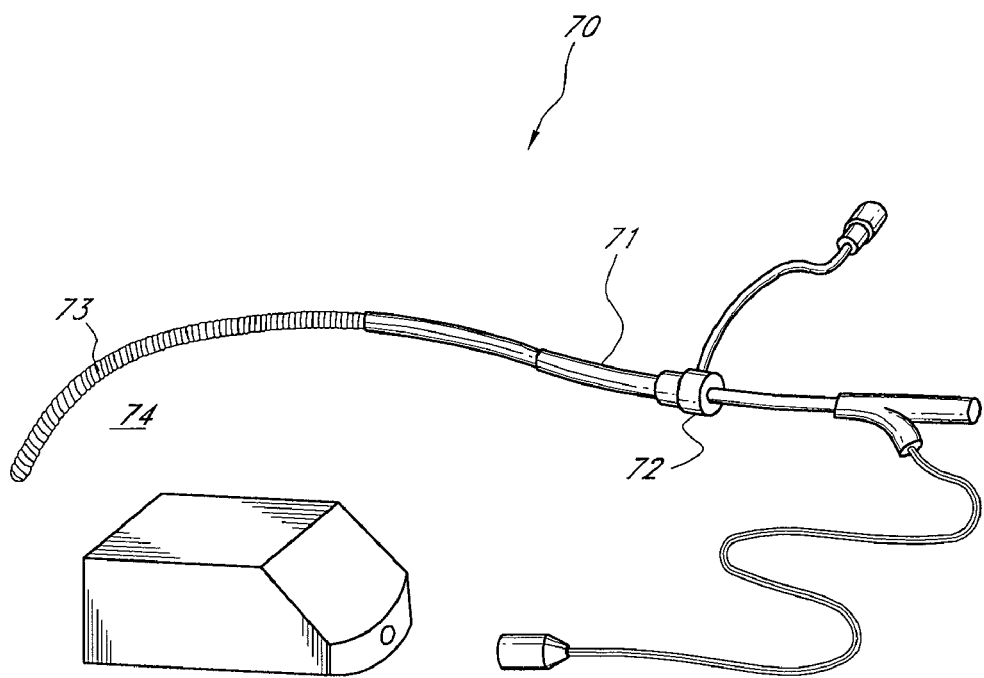
FIG. 14 illustrates an exemplary embodiment of an indexing HAS treatment system.

FIGS. 14 through 18 illustrate embodiments of short-length heating elements and indexing systems. It should also be noted that the devices discussed earlier are also applicable, but for this discussion the coil is used as the preferred embodiment. FIG. 14 illustrates one embodiment of an indexing HAS treatment system comprising an elongate catheter 70 extending through an introducer sheath 71 which includes a hub 72, and a heating element 73 located at the distal end 74 of the catheter 70.

Figure 14A:
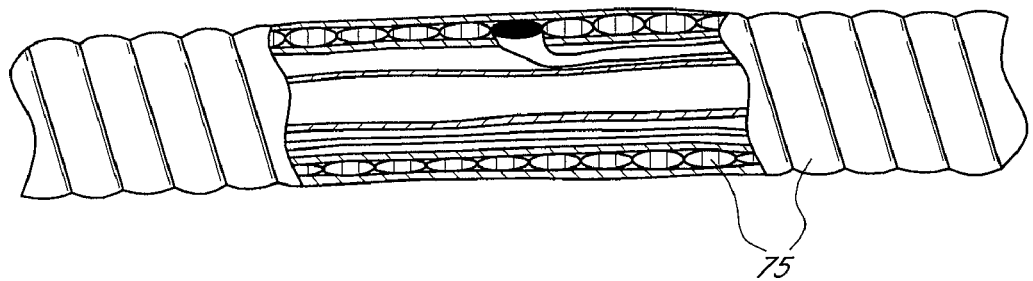
FIG. 14A illustrates a side view of a heating element of the system of FIG. 14 having a portion of a resistive wire removed.

In some embodiments the heating element 73 is an electrically resistive heating element such as those described elsewhere herein. For example, the heating element 73 can comprise a single, bifilar or other electrically resistive wire 75, as shown in FIG. 14A, wrapped in a loose, tight, or variable-pitch coil around a solid or hollow elongate structure. In some embodiments, the heating element 73 has a substantially short axial length. For example, in some embodiments the heating element 73 can be between about 1 and about 10 cm in length. In one particular embodiment, a heating element 73 is provided with an axial length of about 1 to 10 cm, as this range of length is believed to be particularly advantageous for use with external compression applied by hand, when the delivered heating energy less than about 100 W and preferably is in the range of 5-20 W maximum, and when used in combination with an indexing system.

In order to accurately index the heating element by a desired amount, it is desirable to provide a means for repeatedly moving the heating element proximally by a desired distance. In some cases, this desired distance is less than the overall length of the heating element in order to effectively double-treat regions that may receive less heat energy as a result of an uneven heating profile along the axial length of a heating element. It may also be desirable to double treat a portion of an initial and/or final treatment region in order to arrange for the indexing distances to correspond with catheter shaft markings or to arrange that after the full series of indexed treatments the final treatment region is in alignment with the end of the introducer sheath. In addition, it is desirable to have a means for preventing the heating element from being powered up while it is within the introducer sheath. Some examples of embodiments achieving these goals will now be described with reference to FIGS. 14 through 18.

Figure 15:
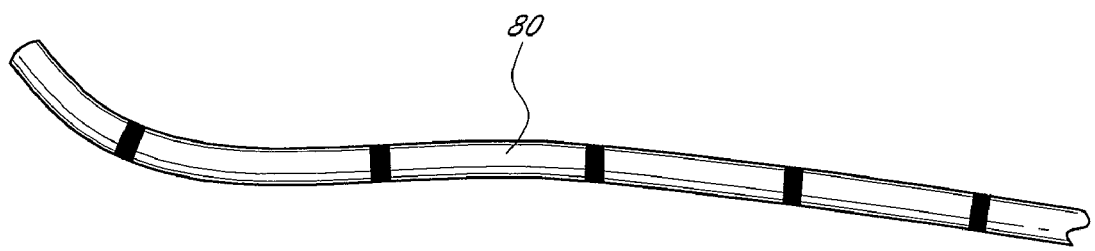
FIG. 15 illustrates an exemplary embodiment of a catheter useable with an embodiment of an indexing HAS treatment system.
Figure 16A:
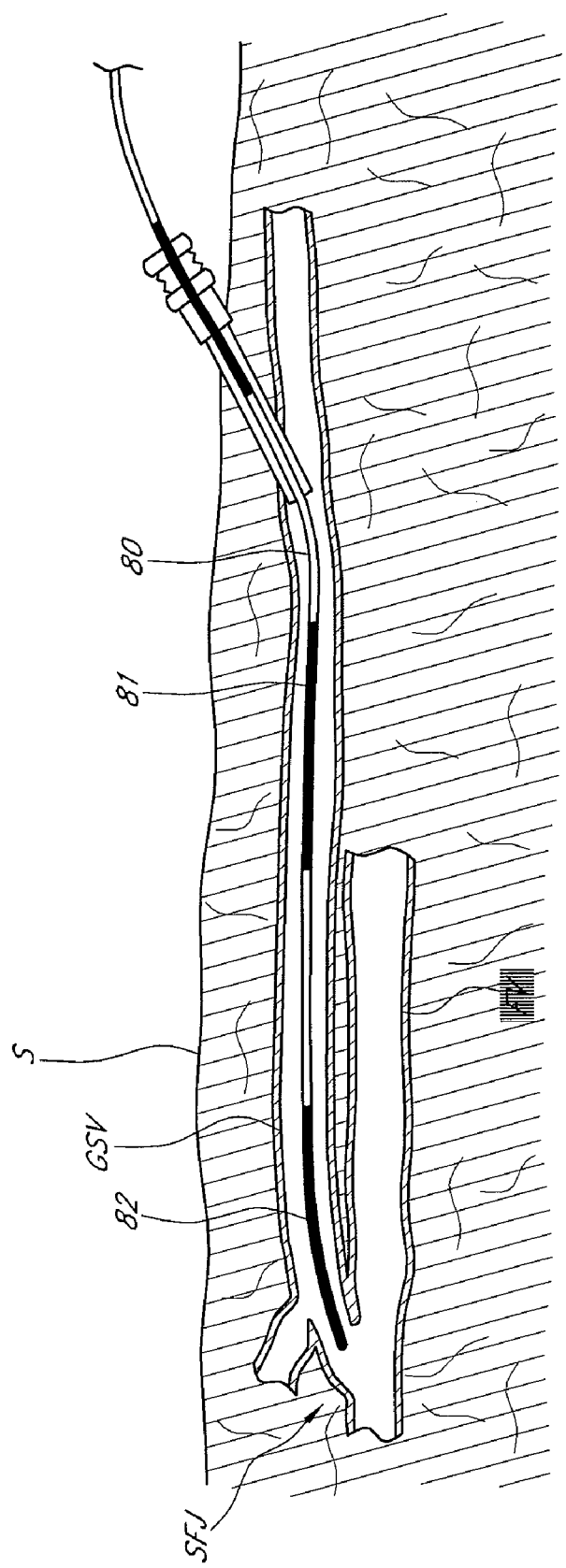
FIGS. 16A-16D, illustrates another exemplary embodiment of a catheter useable with an embodiment of an indexing HAS treatment system.
Figure 16B:
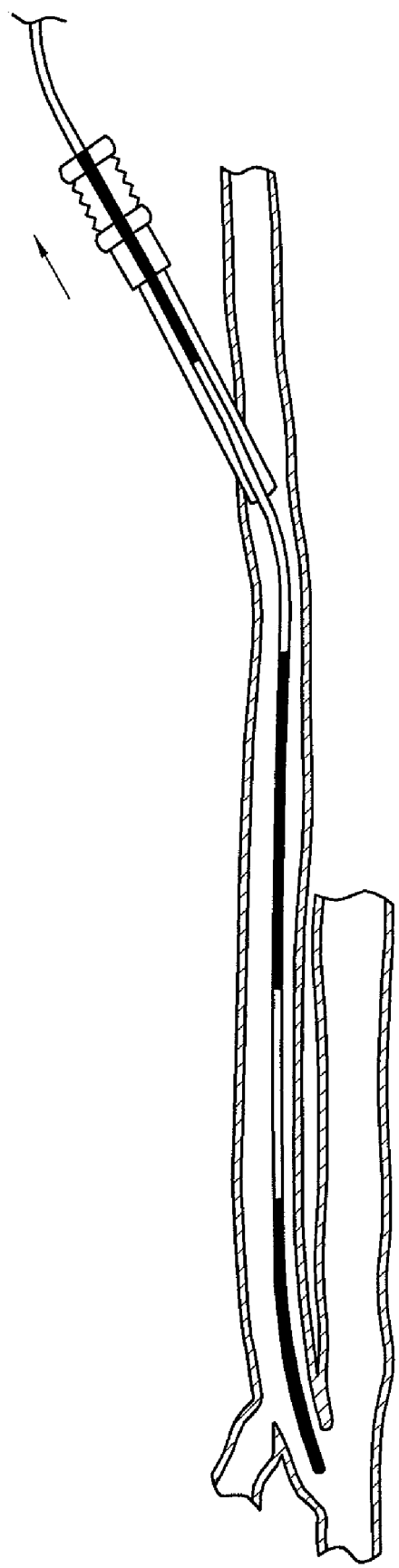
Figure 16C:
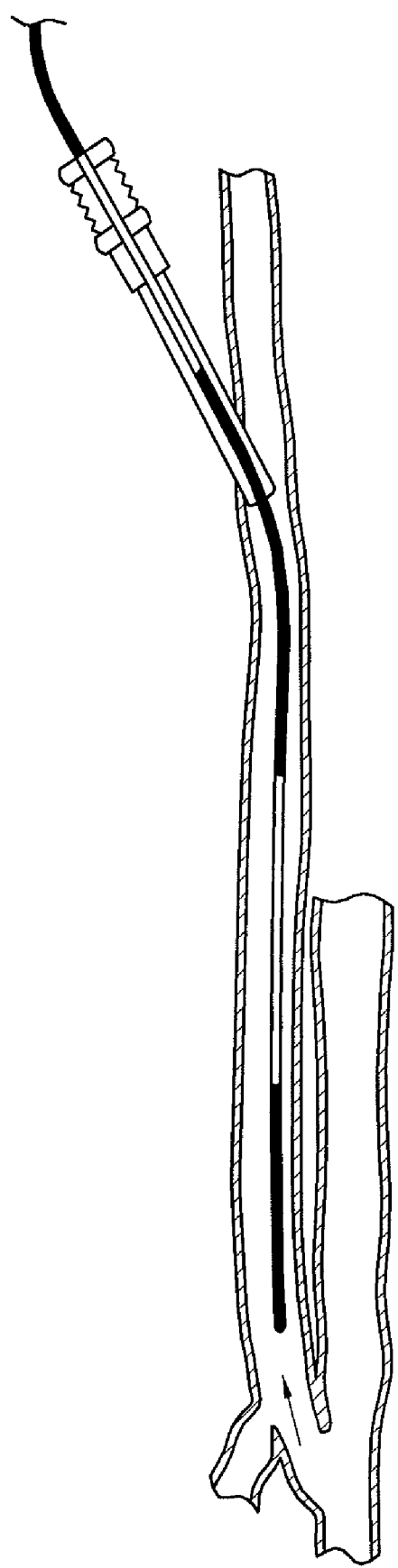
Figure 16D:
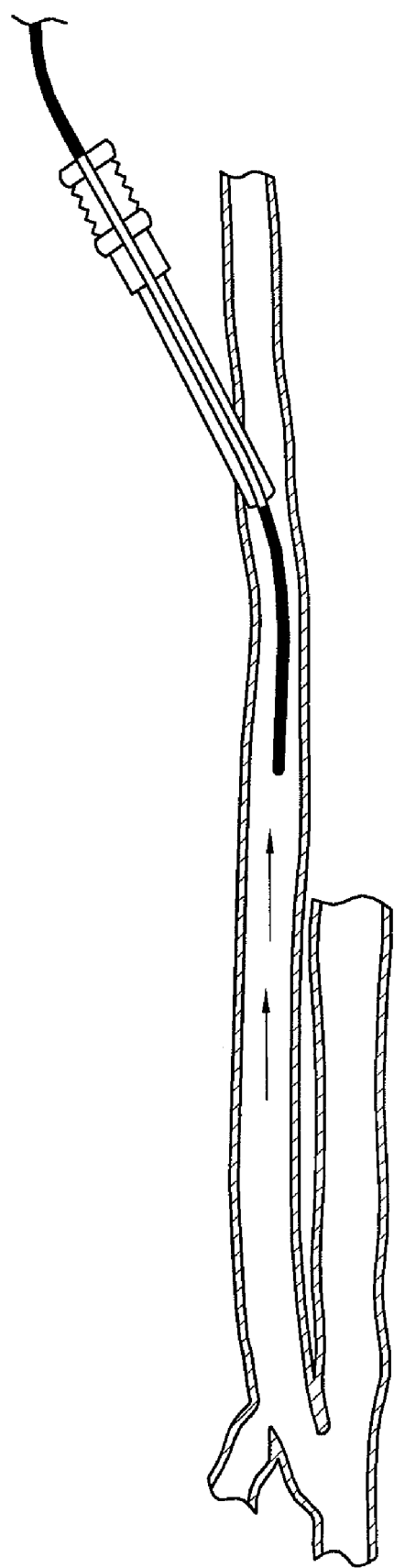
Figure 17:
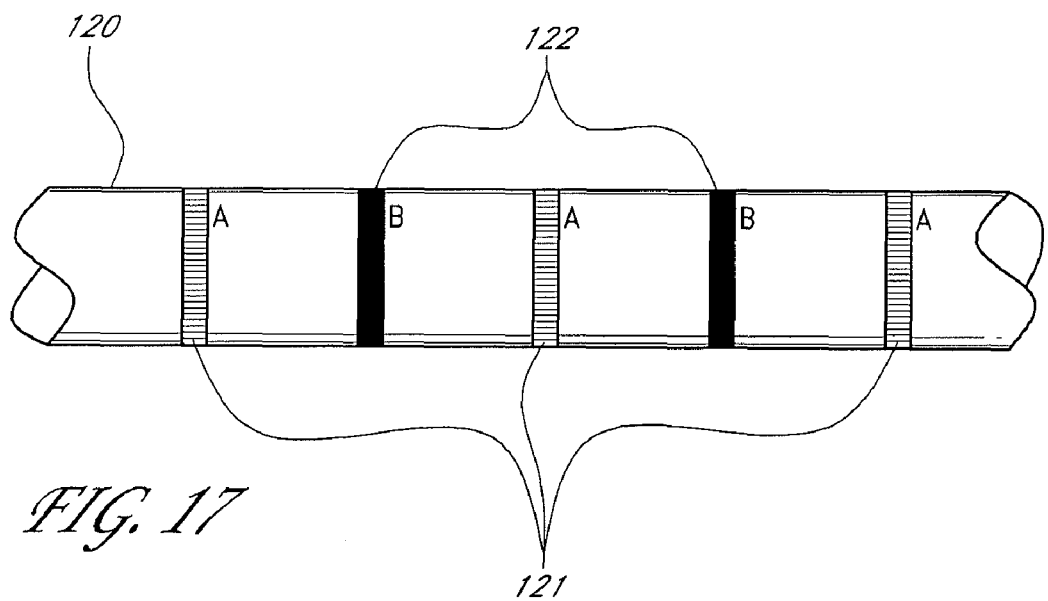
FIGS. 17 and 18 illustrate exemplary embodiments of markings usable for visual verification of indexing positions.
Figure 18:
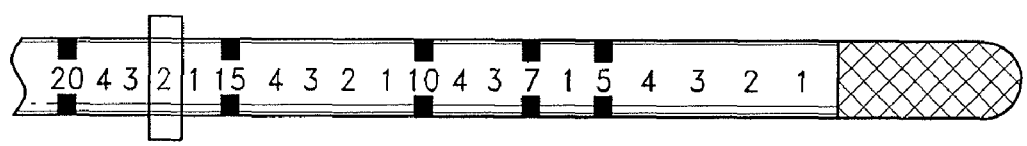

In some embodiments, as illustrated for example in FIG. 15, the elongate catheter 80 can comprise a plurality of markings along its axial length in order to assist in visual verification of indexing positions. For example, in some embodiments such as FIG. 16, the markings 81 comprise alternate colored or cross-hatched sections, each section having an axial length approximately equal to the axial length of the heating element 82, less any intended overlap distance between treatments. In alternative embodiments, as shown in FIGS. 17 and 18, the markings comprise regularly-spaced lines or tick-marks at intervals corresponding to the indexing locations. In some embodiments it may be desirable to provide a unique marker to indicate a final proximal-most indexed position so that the heating element remains spaced from the introducer sheath by a sufficient distance to prevent the sheath from melting.

FIGS. 19 through 35 illustrate embodiments comprising a catheter shaft with a plurality of marks for manually or visually identifying respective indexing positions. For example, the marks can be spaced at one-centimeter intervals. For example the major increments of about 5 centimeters can have numbers which increase proximally along the shaft. In use, the catheter can be indexed by moving it a known distance determined by reading the centimeter markings. In some embodiments, the initial two treatments may overlap by as much as nearly the full length of the heating element, which is acceptable. Increments may be in fractional dimensions, such as about 6.5 cm.

Figure 19:
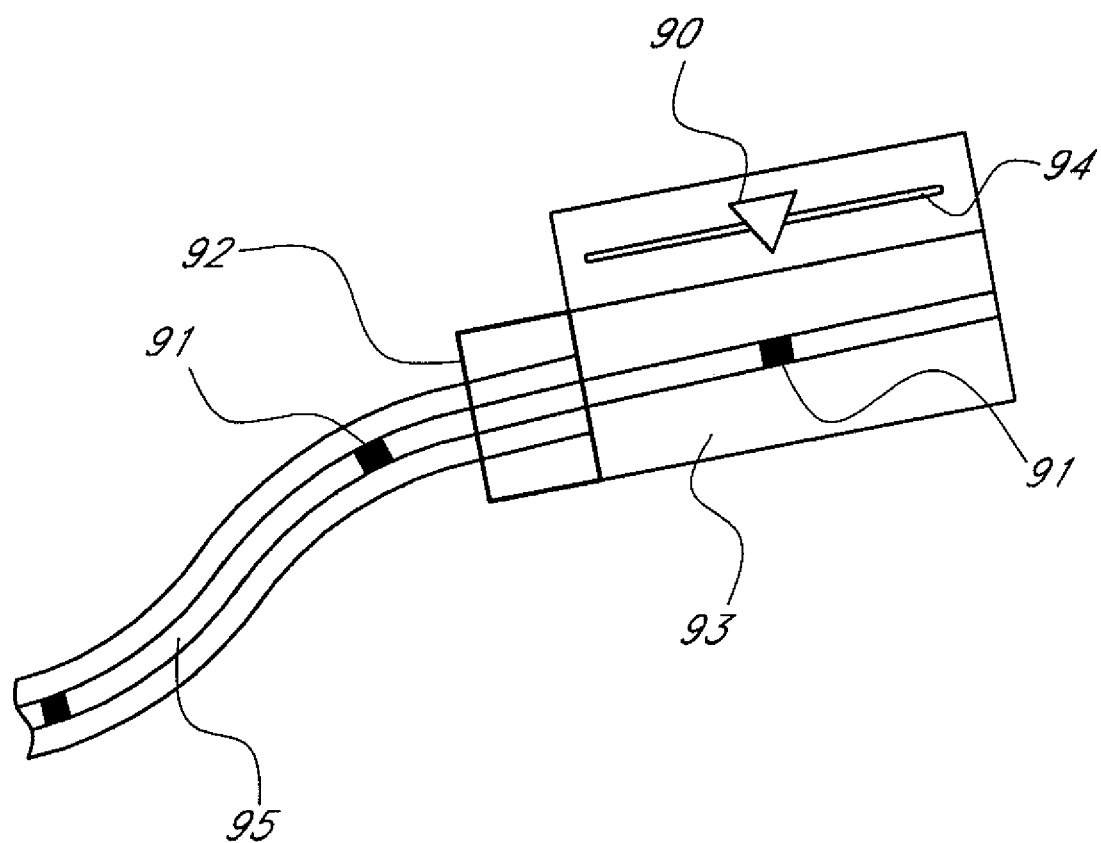
FIGS. 19 and 20 illustrate exemplary embodiments of a movable datum device.
Figure 20:
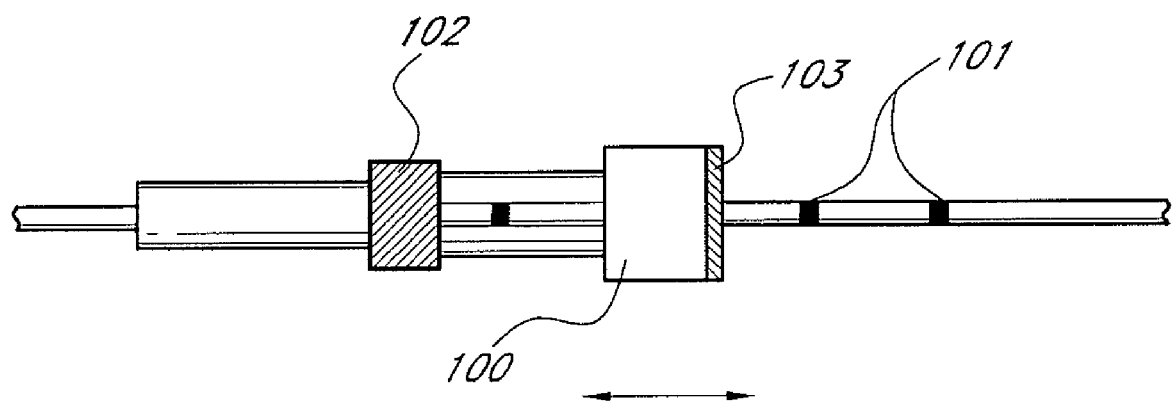
Figure 21A:
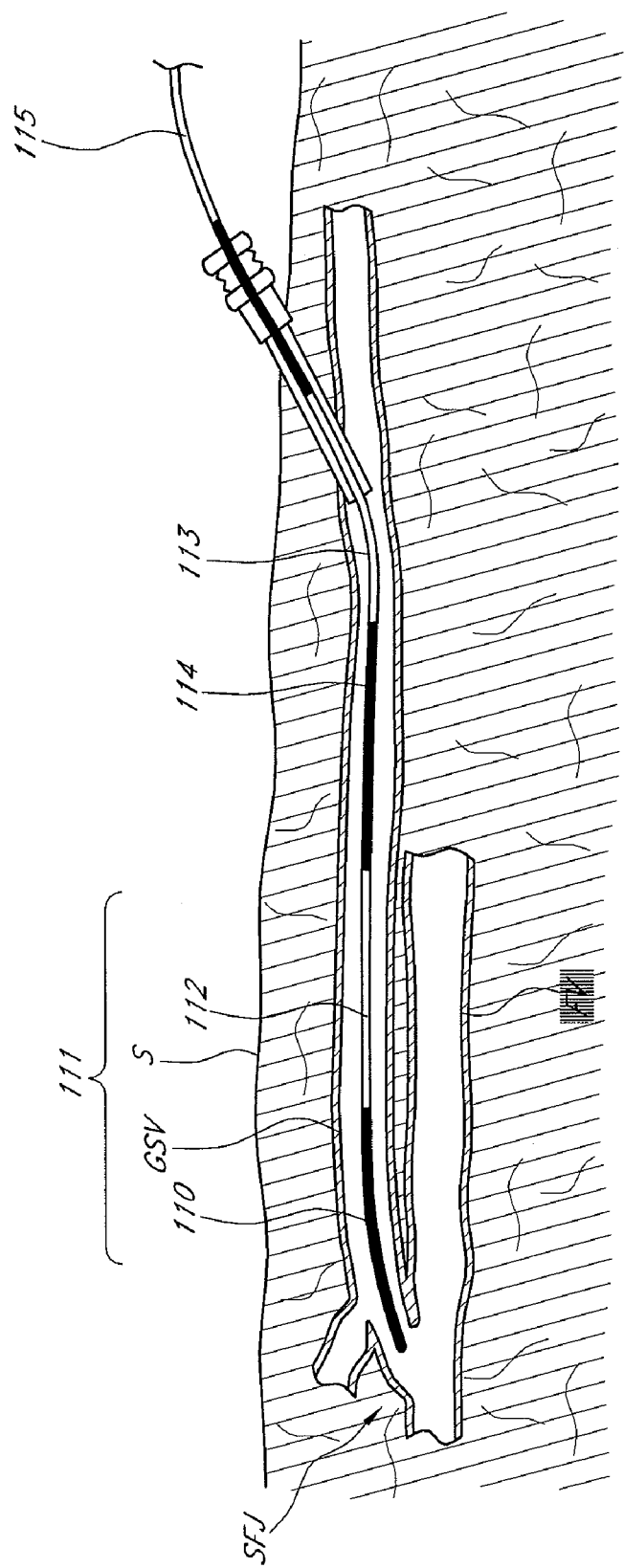
FIGS. 21A-21D, illustrates another exemplary embodiment of an indexing system.
Figure 21B:
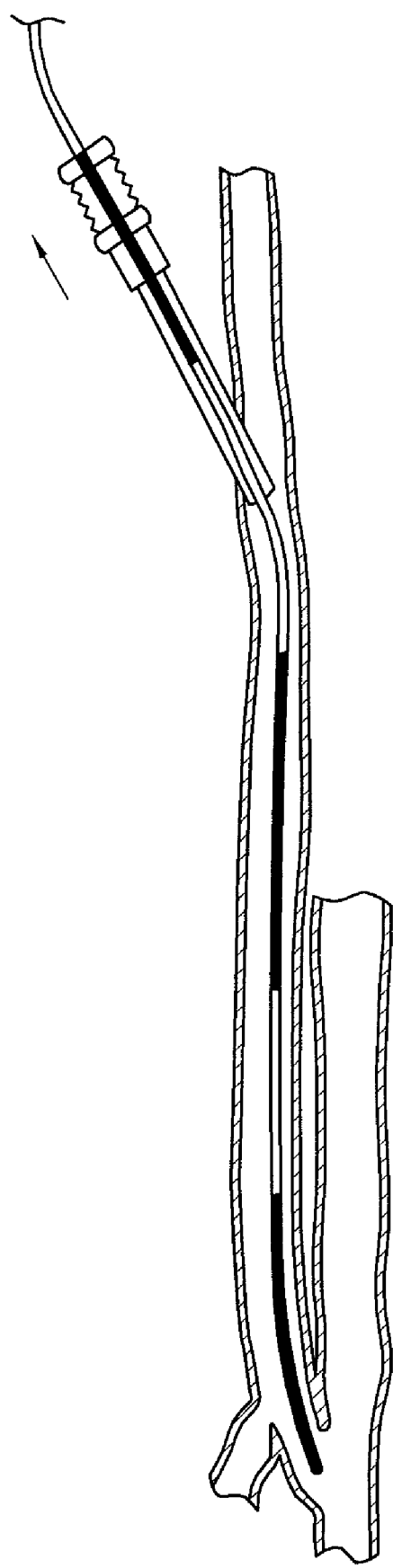
Figure 21C:
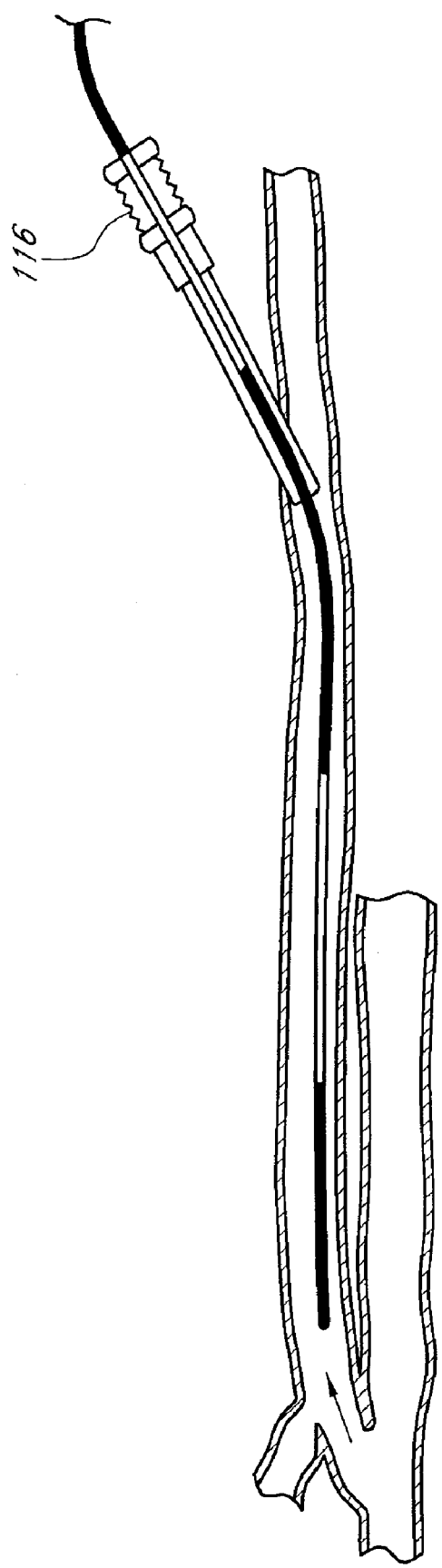
Figure 21D:
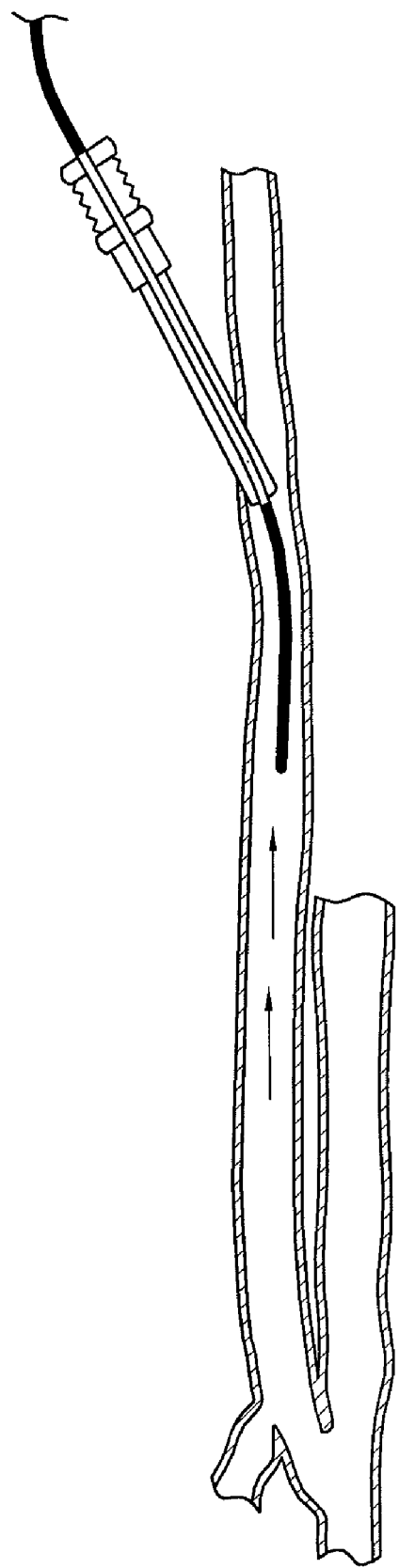

Each of the embodiments in FIGS. 19 and 20 comprises a movable datum device for establishing a starting position for a first treatment. For FIG. 19, prior to a first heating treatment, the datum device 90 is adjusted to point at the nearest catheter shaft mark 91. This gives the physician a starting point so that a fixed-length or measured-length index step can be performed by aligning the catheter markings with the datum pointer 90. Without an adjustable datum pointer 90, tracking fractions of centimeters can be confusing especially when other events are occurring.

FIG. 20 illustrates an embodiment comprising an axially adjustable sleeve 100 provided adjacent to the proximal end of the catheter and mountable to the introducer sheath hub 102. The adjustable sleeve provides an adjustable datum 103 or starting point from which each successive indexing position can be measured in order to prevent the final position from entering the sheath.

FIG. 19 illustrates one embodiment which uses an introducer hub 92 as an attachment point for joining a datum device 93. The sleeve or body 93 has a slot 94 which runs in the axial direction of the sleeve or body 93 and ends near each before each edge so that it is an enclosed slot. A pointer device 90 is slidably positioned within the slot 94. The pointer 90 is preferably mounted within the slot such that there is substantial resistance to sliding, so that it can maintain its position as a reference. The sleeve or body 93 is clear or cut-away so the index marks 91 on the catheter 95 can be seen as they approach the datum pointer 90.

An alternative embodiment comprising a slideable datum pointer is illustrated in FIG. 20. In this embodiment, the tubular sleeve 100 attaches directly to the introducer sheath hub 102 and telescopes axially along the longitudinal axis of the sheath hub 102. The sleeve 100 can attach to the hub with threads or an interference fit so that it will maintain its location relative to the hub 102 during use. The proximal end 103 of the sleeve 100 of this embodiment acts as the datum pointer. The sleeve 100 is preferably clear so that each catheter mark 101 can be seen as it approaches the datum mark 103. The datum mark 103 may also be a colored line along the edge of the sleeve.

FIG. 21 illustrates an embodiment of an indexing system including a catheter with a heating element 110 at its distal end. According to this embodiment, the distal section of the catheter shaft 111 located just proximal of the heating element 110 comprises a unique marking 112 to indicate the "stop treatment zone." In some embodiments, the unique stop-treatment marker 112 comprises a band of a solid or patterned color such as red, yellow or other color or pattern that contrasts with the base color or pattern of the catheter shaft. The stop treatment marker 112 preferably has a length that is substantially equal to the length of the introducer sheath. In practice, introducer sheaths are provided in several known lengths (e.g., 5, 7 and 11 cm introducer sheaths are commonly used). Thus, in some embodiments, it may be desirable to provide several distinct stop-treatment markers corresponding to the various lengths of introducer sheaths. FIG. 21 also shows a similar slideable datum indicator as previously mentioned in FIG. 20. In this version, the datum mark 103 is on an accordion like sleeve 116.

In use, if the stop-treatment marker 112 is pulled proximally out of the proximal end of the sheath, the user will know that the heating element is positioned within the introducer sheath. The user can then push the catheter distally until the stop-treatment marker is hidden within the hub of the introducer sheath.

Figure 22A:
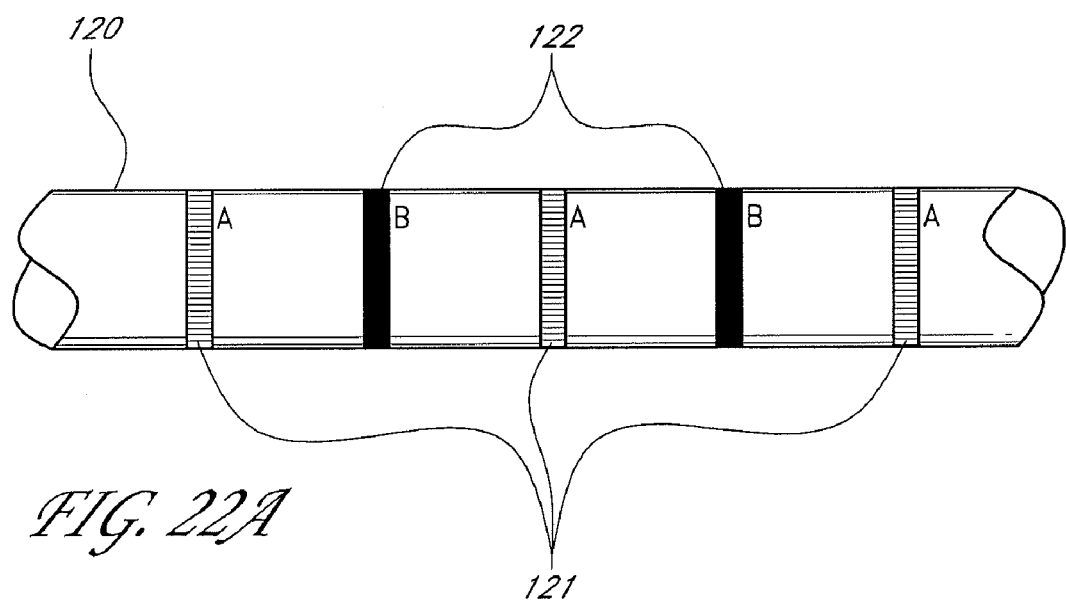
FIGS. 22A-22C illustrate other exemplary embodiments of markings and/or systems usable for visual verification of indexing positions.
Figure 22B:
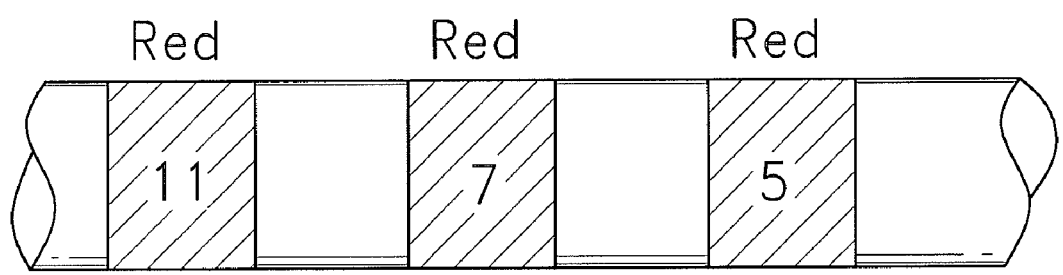
Figure 22C:
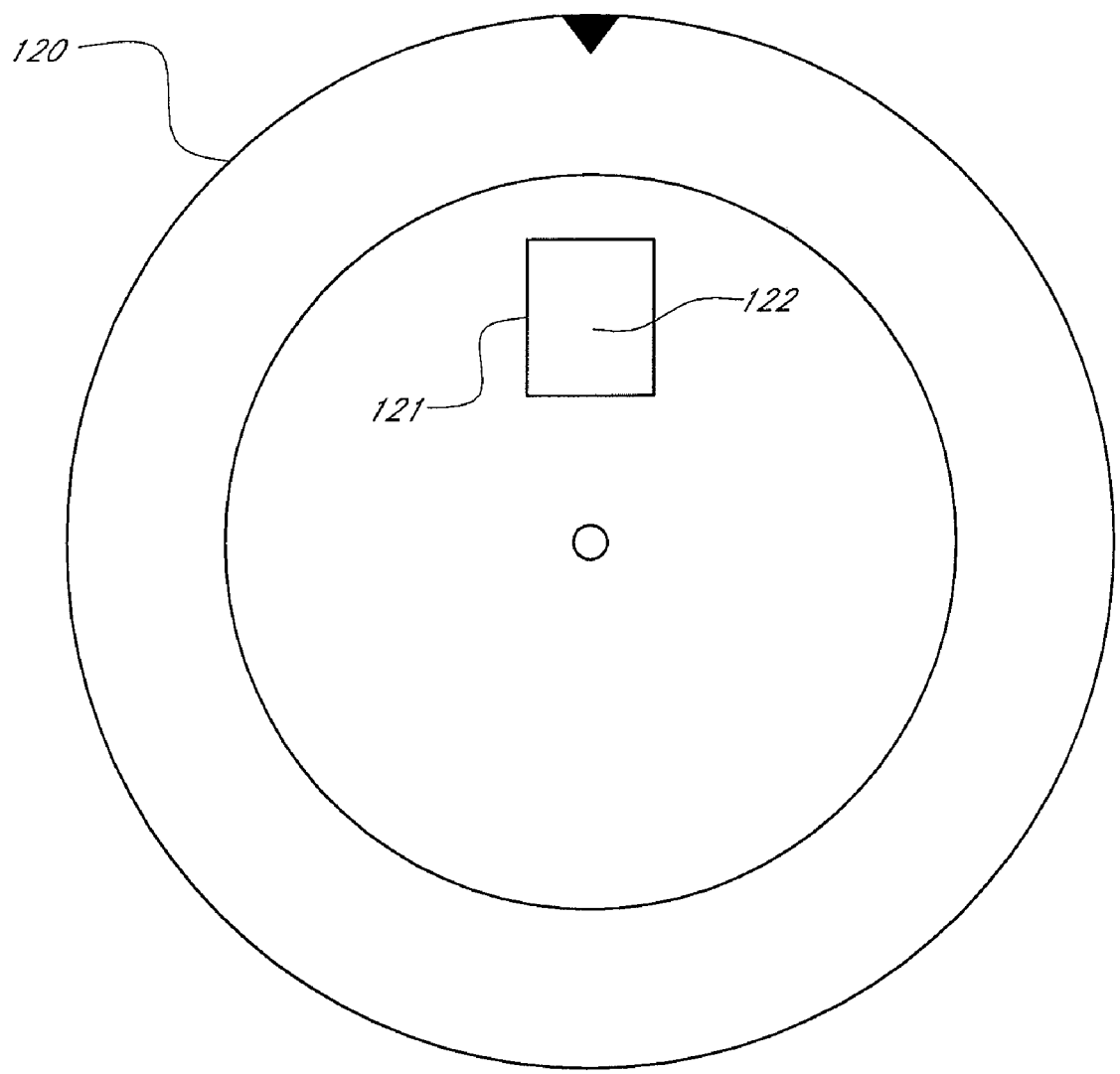

In alternative embodiments, with reference to FIG. 22A, additional markers can be provided on the catheter shaft 120 proximally of the stop-treatment markers 112 as shown in FIG. 21. The markers of this embodiment are generally configured to simplify the indexing process by removing the need for counting individual centimeter-spaced markers. The additional markers 121 and 122 can comprise alternating colored segments or alternating dark/light segments. For example the marks can alternate from blue to white as in FIG. 22B. The alternating markers can also include symbols, numbers, letters such as "A" and "B," as shown in FIG. 22A, or other marks in order to further distinguish the indexing positions. The lengths of the alternating segments are preferably substantially equal to the distance of the index steps. In some embodiments, the index steps are approximately equal in length to the length of the heating element.

Alternatively, the stop-treatment markers on the catheter shaft can be arranged such that the index step marks are actually shorter than a length of a heating element. This encourages intentional overlapping of indexed treatments. For example, for a heating element length of about 7 cm, the shaft markers can be arranged to indicate a 6.5 cm index step. This can create a substantially consistent ½ cm treatment overlap.

In use, the catheter of this embodiment is placed within an HAS at a desired treatment position for an initial treatment. When treatment is about to start the physician notes which catheter shaft color segment is adjacent to the introducer sheath hub. If the initial shaft marker segment is a first color (e.g. blue in the above example) then the index step for the second treatment is at the start of next blue mark on the catheter shaft. Thus, the physician can pull the catheter proximally for the full length of one white segment. If only a partial length of the visible segment initially extends out of the hub, then the physician can simply perform a partial-length index step after the initial treatment, as it is not believed to be detrimental to double-treat a short section of the HAS. Alternatively, the alternating shaft markers 113 and 114 as shown in FIG. 21 can have a length equal to half of the index length in order to reduce the length of a double-treated section, thereby speeding the overall process. Alternatively, one of the adjustable datum embodiments (FIGS. 19 and 20) above can be used to create a new datum point such that the second treatment is a full index distance from the initial treatment. Alternatively a double treatment can be performed at the beginning and/or at the end of the treatment procedure (i.e. during the final treatment increment).

Figure 23A:
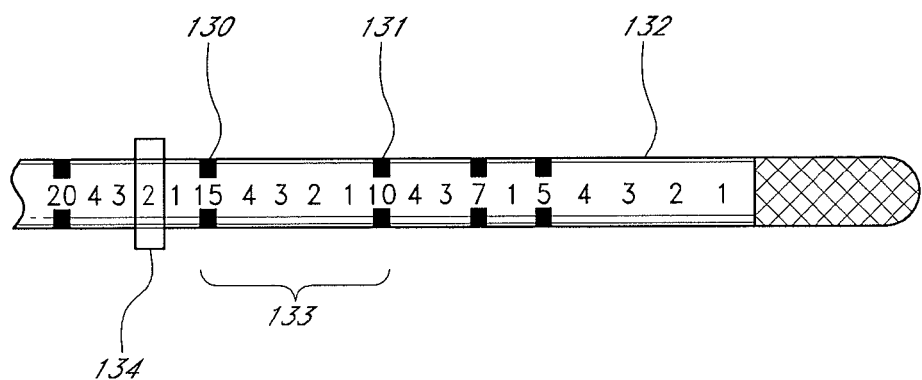
FIGS. 23A and 23B illustrate an embodiment of the invention using printed markers arranged in a repeatable pattern.
Figure 23B:
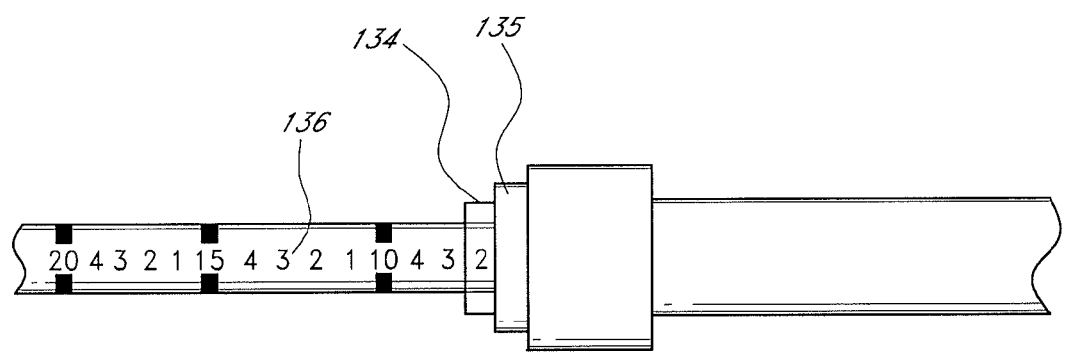

Another embodiment, illustrated in FIGS. 23A and 23B, comprises printed markers arranged in a repeatable pattern for ease of indexing. For example as mentioned above the major 5 cm marks 130 and 131 can have printed numbers increasing proximally along the main body shaft 132. Between these major marks 130 and 131 there can be centimeter marks 133 using a repeated group of the numbers such as 1, 2, 3 and 4 or letters such as A, B, C and D. Additionally, the shaft can have a pair of movable position-indicating sleeves, preferably clear, one of which is shown as 134. As shown in FIG. 23B, the proximal-most position-indicating sleeve 134 can be placed against the introducer hub 135 marking the initial shaft marker-number for indexing. If for some reason the procedure was interrupted such that the physician forgot where he started and what the index datum was, the position-indicating sleeve 134 can provide this information. The sleeve may indicate this as it is able to stay in place due to the friction fit even when the catheter is temporarily removed from the introducer sheath. When it is replaced or the physician comes back to continue treatment the sleeve will still be in place. The sleeve in place against the introducer hub will imply that the next treatment step is the next identical proximal marker-number 136.

In an alternative embodiment, illustrated for example in FIG. 24, a secondary sheath 140 may be provided and held in place by a compressible o-ring type seal 141 (e.g. a Touhy Borst adapter) located at the proximal end of the secondary sheath 142. In its initial position, the device 143 has the secondary sheath 142 moved forward so that the distal end 145 is up against the distal therapeutic section 144, which is configured to limit travel of the secondary sheath, such as being stepped in an increased diameter or by providing a physical stop at the distal end such as a ring attached to the proximal end of the therapeutic section 144. In one embodiment, the secondary sheath 142 is shorter in length than the main body by one index section.

Figure 24A:
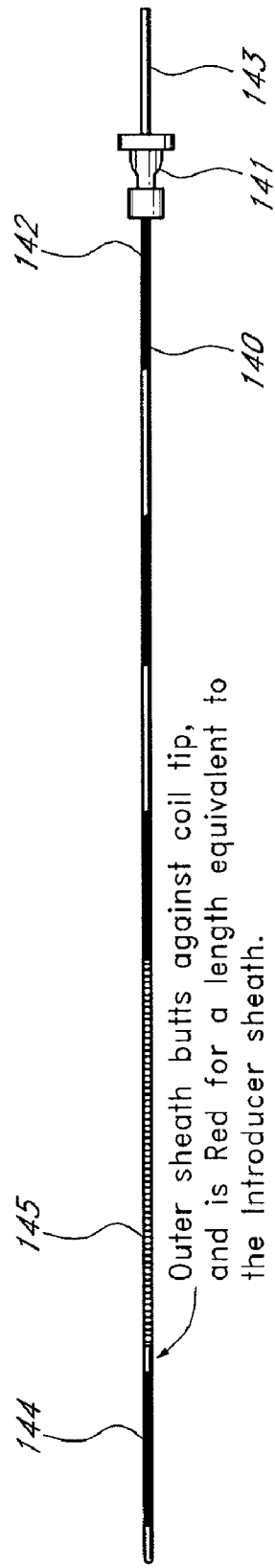
FIGS. 24A-24D, illustrates another exemplary embodiment of an indexing system.
Figure 24B:
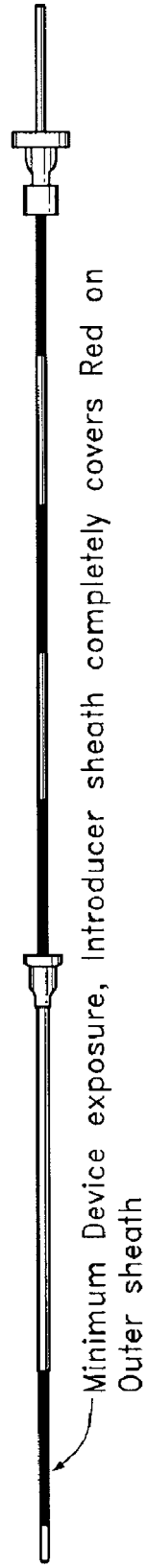
Figure 24C:
Figure 24D:
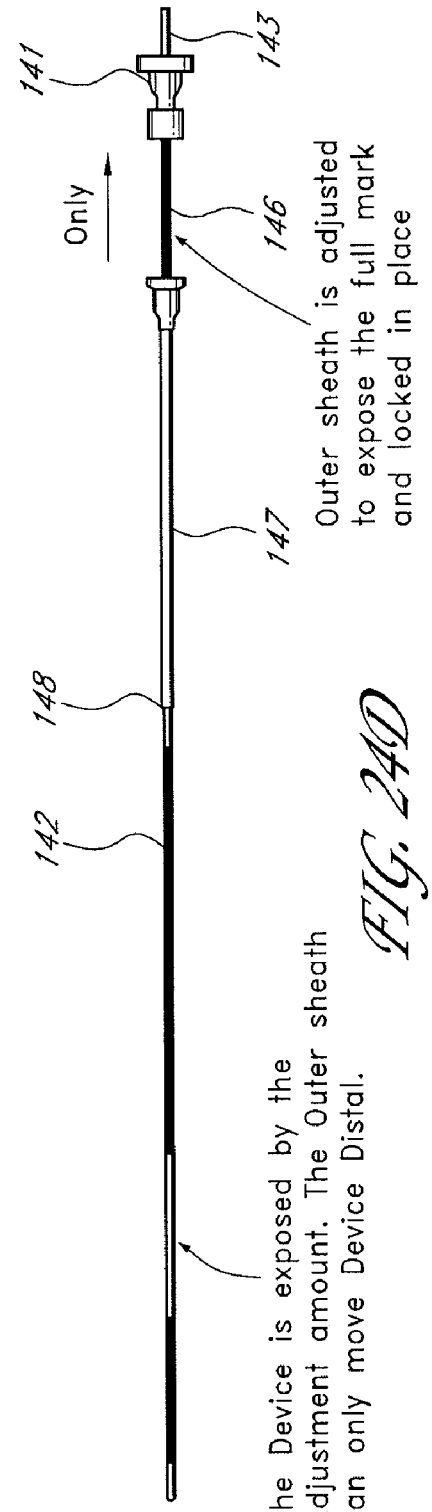

Just prior to the initial treatment, as shown in FIG. 24D the secondary sheath 142 is adjusted until the change in color segments 146 becomes apparent. In an embodiment, this means the o-ring 141 on the secondary sheath 142 is loosened and then moved proximally while the main body catheter 143 and the introducer sheath 147 remain stationary. Once the secondary sheath 142 is at the index step color transition, the o-ring 141 is tightened. This gives the physician a starting point so that a full index step can be easily done. An untreated section can occur at the end of the HAS adjacent to the introducer tip 148.

Figure 25A:
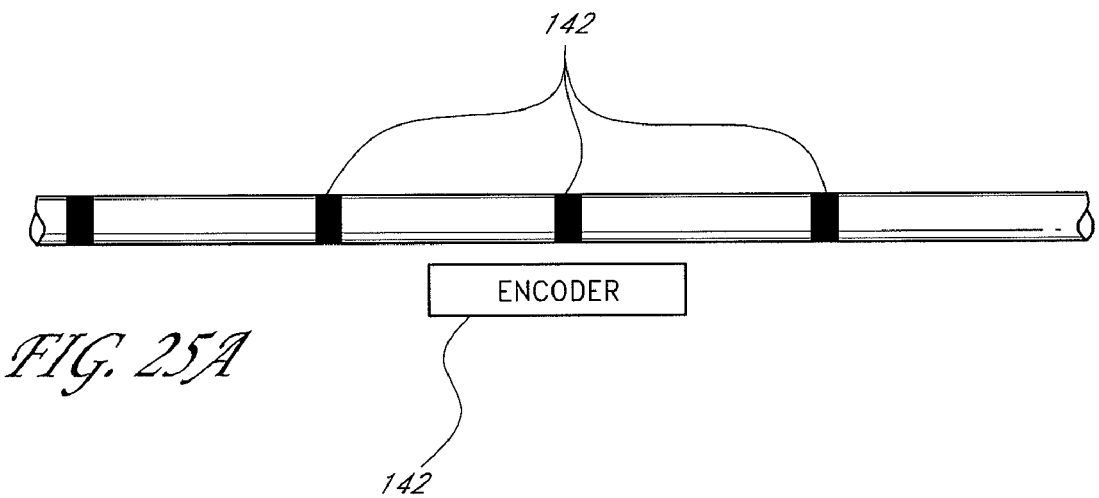
FIGS. 25A and 25B illustrate other exemplary embodiments of an indexing system.

FIG. 25A illustrates an embodiment of an indexing system configured to facilitate the regular positioning of the heating element during each indexing step by providing automatic verification of a catheter position within the HAS without requiring manual visual or tactile verification of the catheter position by the physician. For example, a plurality of mechanically or electrically detectable markers can be used to indicate to a physician that an indexing position has been reached. For example, a plurality of printed magnetic ink marks can be provided on the catheter shaft 150. A magnetic reading sensor 151 can be placed adjacent to the introducer hub, and joined to a controller configured to produce an audible or visible alert when each magnetic marker passes underneath the sensor. This system allows for the index distance to be tracked and indicated to the physician visually and or audibly on the generator without requiring the physician to visually watch markings on the catheter.

Figure 25B:
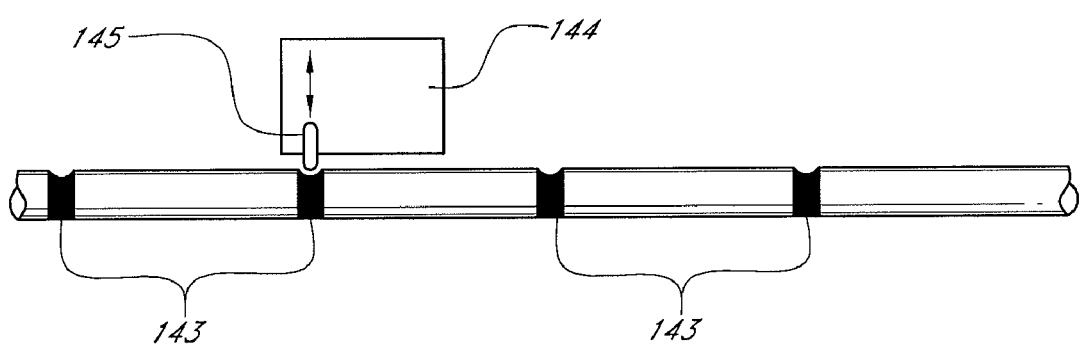

In an alternative embodiment, FIG. 25B shows a device that uses a set of detents 143 along the catheter main body shaft. The locator 144, figuratively shown in FIG. 25B, fits over the catheter main body shaft. The locator may also attach to the introducer hub in order to hold it stationary. As the catheter is moved proximally, the follower 145, which may comprise a spring loaded cam, may click into a detent when it slid under the tip of it. This would provide an audible and tactile resistance indicating proper index placement. The follower 145 may be a switch connected to the system controller. This switch may tell the system the catheter has been indexed to the next position. The system controller may also alert the physician that the catheter is ready for treatment by audible and visual indicators.

In an alternative embodiment, illustrated for example in FIG. 26, a temperature sensor 151 (such as a thermocouple an RTD (resistive temperature device) or a set of contacts that measure resistance) may be placed on the shaft 150 of the catheter at a position proximal to the heating element 152 by a distance equal to the length of the introducer sheath 153. Accordingly, a control system 154 may be located within the power source or otherwise in electronic communication with the sensor. The control system 154 may monitor the temperature of the sensor 151 during treatment. When the sensor 151 notes a significant drop in temperature relative to the patient's body temperature (e.g. a drop to room temperature) caused by the sensor 151 leaving the HAS and entering the introducer sheath 153, the system alerts the physician that the treatment is complete. Such an alert may be in the form of a visible light, and audible sound or another alert signal.

In the embodiment of FIG. 27, the catheter distal section 74 comprises two temperature sensors 160 and 161 on the catheter 74. A first sensor 160 is positioned at or near the distal end 162 of the heating element 163, and the second sensor 161 is positioned at or near the proximal end 164 of the heating element 163. In embodiments in which the heating element 163 is an electrically resistive coil, "near the end" can mean that the temperature sensor 160 or 161 is positioned in the coil winds, such as about one-quarter to about one-half of a centimeter from the end of the coil. In certain embodiments, the temperature sensors 160 and 161 are preferably joined to a control system 165 configured to determine the temperature at each point and to compare these values with one another.

In use, the catheter 74 of FIG. 27 may be placed in an HAS at a desired initial treatment site, which can be located using any available technique. Energy can then be applied to the HAS in an initial treatment step. After the initial treatment, the device is moved proximally, during which time the control system 165 monitors the temperatures sensed by the two sensors 160 and 161. The section of the HAS treated in the initial step will be at a higher temperature than the surrounding portions of the HAS. A significant drop in the temperature of the proximal sensor 161 relative to the temperature of the distal sensor 160 implies that the heating element has been moved proximally out of the previously-heated region. Similarly, a significant drop in temperature (i.e., back toward body temperature) detected by the distal temperature sensor 160 indicates that the coil has been indexed to the next adjacent treatment position. The power source can be manually activated or programmed to automatically engage power once the heating element 160 reaches its next indexed position.

By placing the temperature sensors in the coil, the indexed treatments may create an overlap of adjacent treatment sections. In alternative embodiments, the temperature sensors may be positioned at or closer to the proximal 164 and distal 162 extents of the heating element 163 in order to eliminate or reduce the amount of overlap in adjacent indexing positions.

Figure 28A:
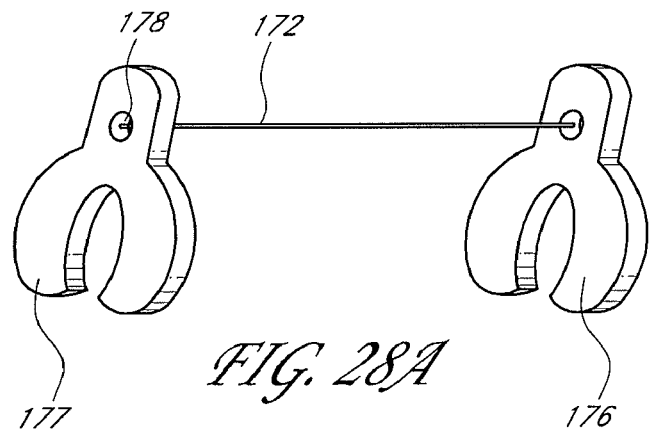
FIGS. 28A-28C and FIGS. 29A-29B illustrate exemplary embodiments of indexing systems for facilitating automatic movement of a catheter.
Figure 28B:
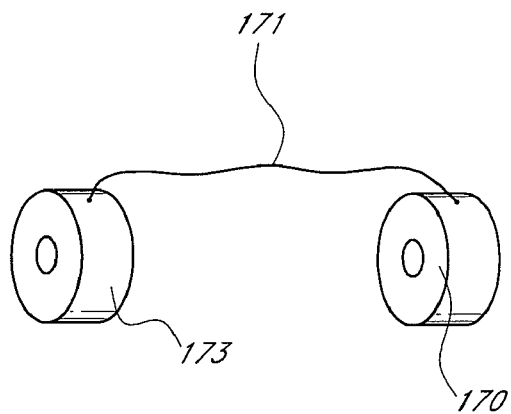
Figure 28C:
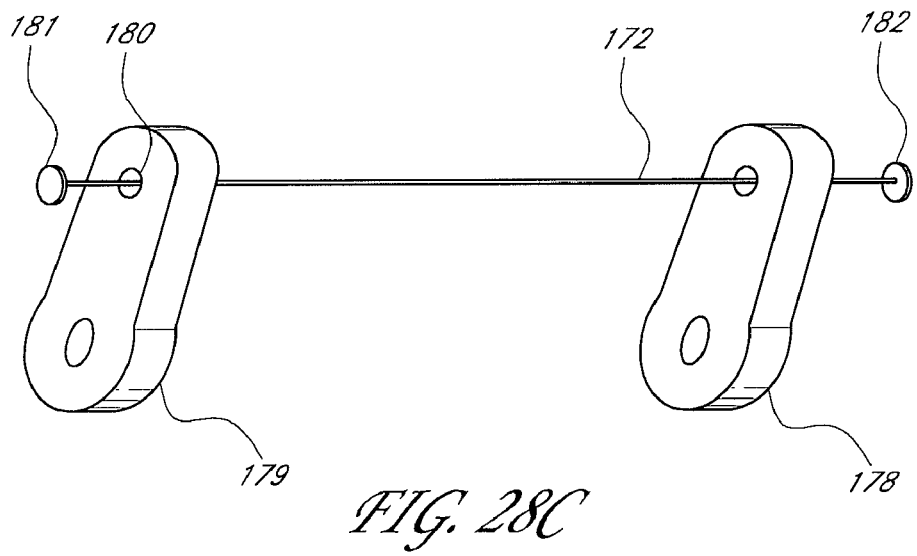

FIGS. 28 and 29 illustrate embodiments of indexing systems configured to facilitate regular indexing movements of the catheter without requiring the physician to be part of the control system. Also, for example, certain embodiments may facilitate automatic movement of the catheter from one position to the next indexed position without requiring verification of the position by the physician.

Figure 29A:
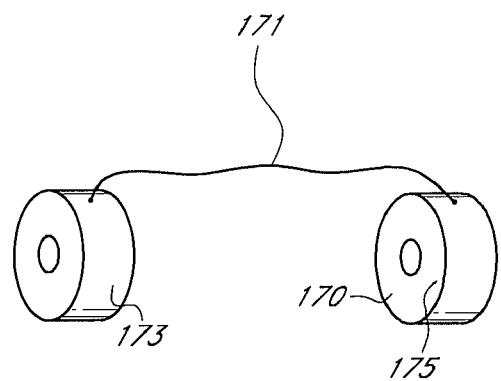
Figure 29B:
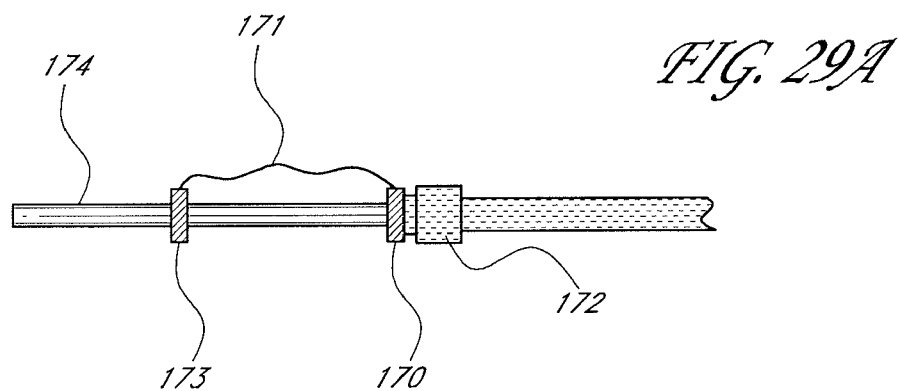

Another alternative embodiment, illustrated for example in FIGS. 29A and 29B, uses a pair of o-ring type donuts 170 movably positioned on the catheter shaft 174 and joined to one another by a string 171 or a rigid sliding rod 172. A first of these o-rings 170 may be attached to the introducer hub 172, while the second 173 is permitted to move axially along the length of the catheter 174, yet with sufficient friction that it may also be used to grip and move the catheter 174 axially.

The system of this embodiment generally operates by movement of the o-rings after a treated section has been completed. In certain embodiments, before moving the catheter, both o-rings 170 and 173 should be placed against the introducer hub 172 by sliding them on the catheter shaft. Next the more proximal o-ring 173 and the catheter shaft are moved in tandem proximally away from the distal o-ring and introducer hub (also in tandem) until its motion is arrested by the string or rod 171 or 172. This places the therapeutic element in a new adjacent section for treatment.

In certain embodiments, the o-ring adjacent the introducer hub can be held against the introducer sheath hub manually.

Alternatively, the first o-ring may be configured to have an interference fit or mechanical luer lock fit in order to attach to the introducer sheath hub.

If the o-rings 178 and 179 shown in FIG. 27C are to be joined to one another by a rod 172, the rod is preferably configured to limit the axial travel of the first o-ring 178 with respect to the second o-ring 179. In this embodiment, the o-rings 178 and 179 may have a tab extending radially outwards with a hole 180 therethrough. The rod 172 may fit through the two holes 180 of both modified o-rings 178 and 179. This rod 172 may have stops 181 on both ends. In one embodiment, the rod ends can resemble flat head nails.

Alternatively, the o-rings 170 and 173 can be shaped like a turkey wish bone. The side legs may fit around the catheter shaft in such a way that it can be easier to slide axially along the shaft than come off of it. An appropriate elastic type of material such as silicone, KRATON®, urethane, or the like can be used so that the component can be pushed onto the shaft and have an interference fit in order to help anchor the component in place until it is manually moved. As previously mentioned, the single short tab of the wishbone can be the extended tab with the hole 178 in it. The string or the sliding stop can use these holes as mentioned above.

Once the catheter is in position so that the heating element is at an initial treatment site, both markers 170 and 173, shown in FIG. 29B, are placed against the introducer sheath hub 172, and the initial treatment is performed. The catheter 174 is then indexed, and a second treatment is performed. After the initial and subsequent treatments, the catheter is indexed back or away from the initial treatment site. The distance indexed is determined or limited by the length of the string or sliding stop. By having the o-ring 170, which is adjacent to the introducer hub 172, remain there during the movement of the catheter 174, the second o-ring 173 moves with the catheter until it is stopped by the string 171 or sliding arm 172. This limit is visually apparent. Once indexed, the unanchored o-ring 173 is repositioned back adjacent to the stationary o-ring at the introducer hub.

Figure 30:
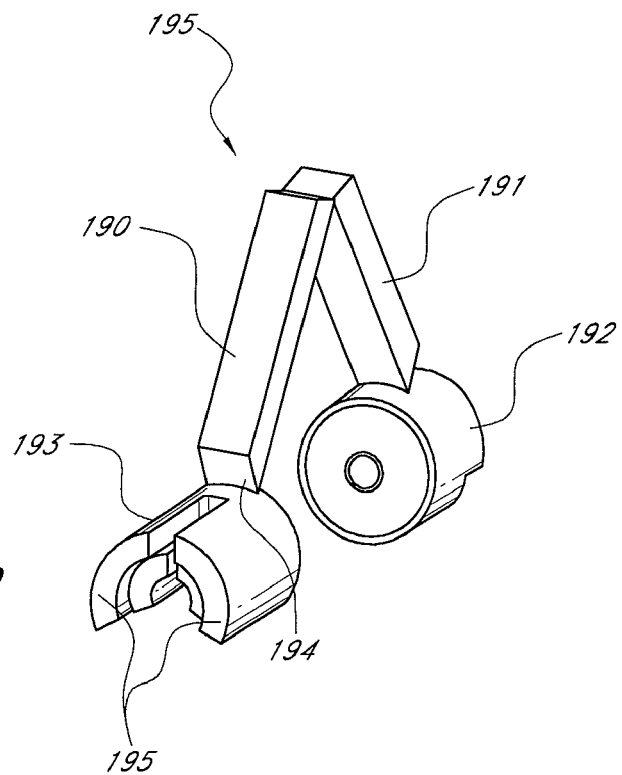

FIGS. 30 through 32 illustrate embodiments employing various linkages to index the catheter by a desired amount. FIG. 30 illustrates a device comprising a linkage with two hinged arms 190 and 191. The linkage arms 190 and 191 are of substantially equal length and hinged together. In certain embodiments, the range of movement of the linkage arms is about 0 to about 180 degrees. The range may be based upon the limit of travel due to the cylinders 192 and 193 coming together (0 degrees) and when the linkage arm ends are tandem (e.g., the inverted "V" is spread open (180 degrees)).

This illustrated linkage 191 is connected to an anchor component 192 which attaches to the introducer hub 172. The linkage 191 to anchor connection may also comprise a hinge. A grip component 193 is attached to the opposite end 194 of the linkage 190. This grip 193 is attached by a hinge connection 194 and is used to maneuver the catheter shaft 174. The linkage 195 may also have a spring or elastic component further linking the two arms 190 and 191 and can keep the device in a preferred position when not in use. Such a preferred position involves the grip component 193 being located adjacent to the anchor 192 and introducer hub 172.

In one embodiment, the grip 193 is a component which straddles the catheter shaft 174, and may be, for example, cylindrical. In one embodiment, the grip 193 is not a complete circle and comprises an open section configured to receive the catheter therein without the need for threading the catheter through the center of the grip 193. In certain embodiments, the hinged end 194 of the linkage arm 190 is attached to an extended set of tabs 195 at one end of the grip 193. The physician can effectively pinch the grip tabs 195 with the thumb and forefinger, which in turn captures the catheter shaft. The inner radial surface of the grip 193 can be, for example, a soft tacky type of silicone or KRATON.

FIG. 31A illustrates another embodiment of a mechanism that is similar to the previous linkage arm 195. In this embodiment, there are two sets of arms 200 and 201, making the device substantially symmetrical. The anchor component 202, which attaches to the introducer hub 172 may be essentially the same as the embodiment of FIG. 30 except that both linkage arms 203 and 204 of this embodiment may be attached to it, and/or these connections can be hinged as well. At least one of the linkage arms 200 and 201 may also have a spring or elastic component to keep the device in a preferred position when not in use. This preferred position is to have the grip component 205 adjacent to the anchor 202 and introducer hub 172.

As previously mentioned, the two linkage arms sets are each made of two rods of substantially equal length, such that all four arms are equal. Each pair is hinged together. The range of movement is preferably about 0 to about 180 degrees, although the device can be limited to narrower ranges as desired.

The grip component 205 may be attached by a hinge for each of the two arms. An alternative embodiment may include a complete cylindrical component that is threaded over the catheter shaft. As shown in FIG. 31B, by use of at least one o-ring inside the grip 205, the double arm linkage can grip the shaft as it was indexed and release as the mechanism returned to the adjacent position next to the introducer hub. The o-ring inside the grip 205 may have an interference fit on the catheter shaft 172. When the grip is moved away from the introducer hub, the o-ring may come against a tapered surface 206, which can cause the o-ring to tighten its fit on the catheter shaft. The tapered surface may be of an angle to accommodate two o-rings 207 of different sizes for improved gripping forces.

For ease of use of this mechanism, in certain embodiments, the apex of both linkage arms may have an additional component 208 that the thumb and finger can push against to make the device work.

Figure 32A:
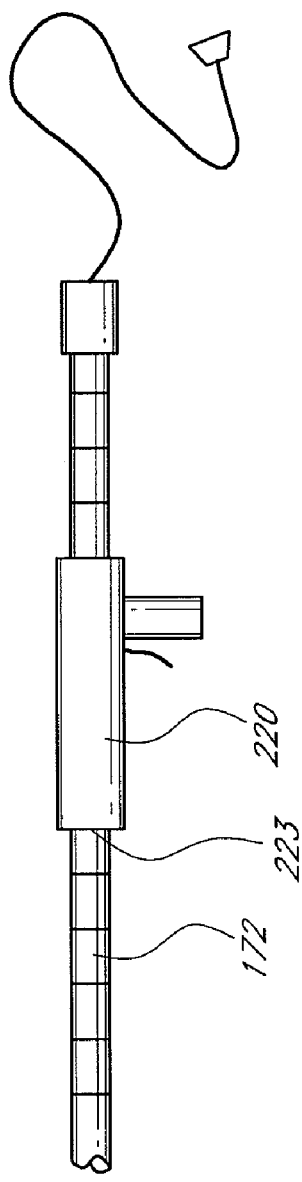

FIG. 32A illustrates another embodiment of an indexing device comprising a mechanical indexing handle 220. This illustrated embodiment of the indexing handle 220 may be threaded over the main catheter body 172 and treated as an accessory. The indexing handle front end 223 may be configured to securely attach to the hub 172 end of an introducer sheath. The introducer sheath can become the stationary basis to index the catheter 172 during treatment of the HAS. This indexing handle 220 can be designed to step the main body of the catheter 172 proximally a set distance relative to the introducer hub.

In the embodiment of FIG. 32A, the accessory handle engages the catheter main body for indexing. In certain embodiments, the catheter cable is connected to the generator in the standard fashion and is separate from the indexing handle. The handle may have a set trigger travel or a set index distance. As the handle is triggered, the mechanism grasps the catheter main body and moves it proximal relative to the handle, which is stationary. At the end of the travel, the handle mechanism then releases the catheter main body and returns to its initial position. In certain embodiments, this mechanism us similar to the o-rings shown is FIG. 31B. Alternatively, the mechanism may be a cam action component which is pushed against the main body tube as it starts its pull back and then is released at the end of the travel or index distance.

Figure 32B:
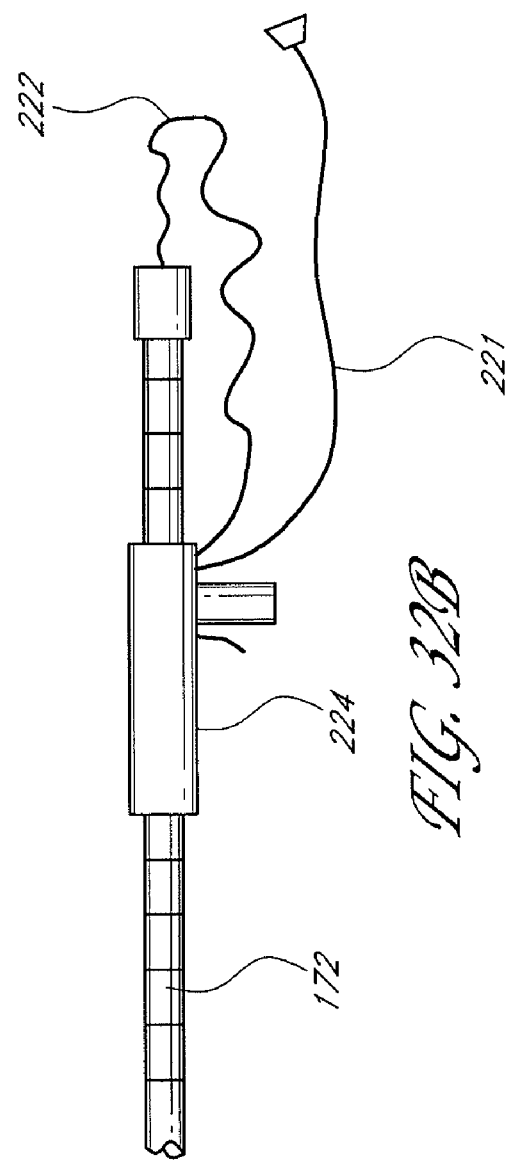

An alternative embodiment of the index handle is illustrated in FIG. 32B, and comprises two cables and is substantially integral to the catheter main body 172. In certain embodiments, the cable 222 extends from the proximal end of the catheter main body to the indexing handle 224. The handle 224 may have one or two switches, such as an OFF button and an ON button to remotely control the power from the generator during treatment as required. Alternatively this may be a toggle switch to combine the two modes. Alternatively, this may be a momentary switch which signals the generator to power up or power down. The handle may have the second cable 221 extending from it and can be designed to connect to the generator.

Figure 33A:
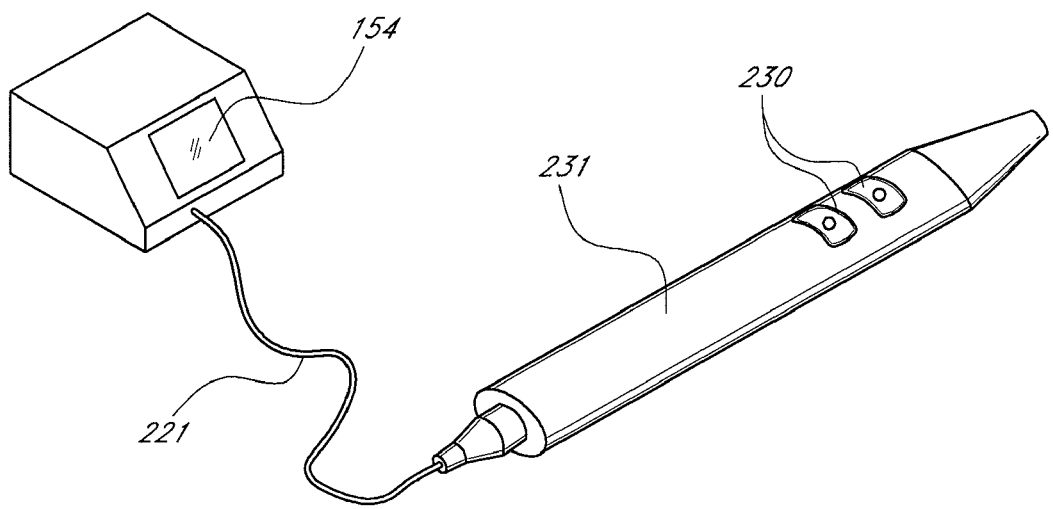
FIGS. 33A-33B and FIGS. 34A-34B illustrate exemplary embodiments of an indexing system having a switch to control power applied during treatment.
Figure 33B:
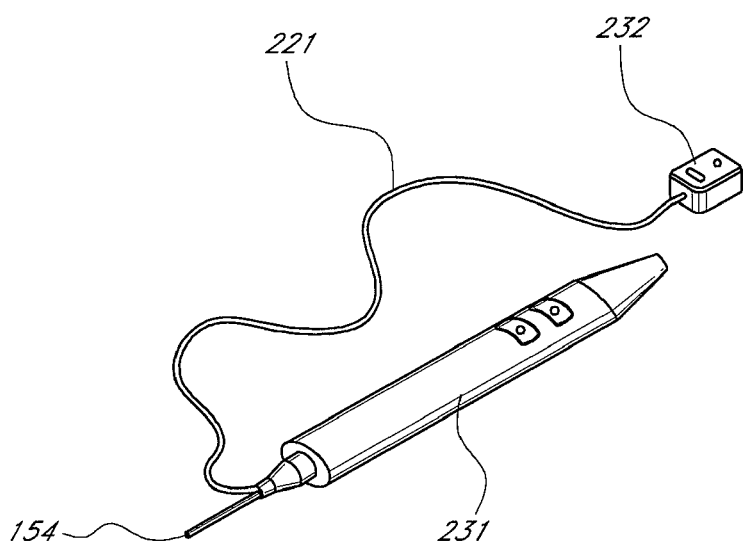

FIGS. 33 through 34 show several alternative embodiments using a remote switch integral to the handle or as a separate remote switch. FIG. 33A shows the buttons 230 integral to the catheter handle 231 and the cable 221 attached to the generator 154. FIG. 33B illustrates an alternative embodiment with the remote switches 232 separate from the catheter handle 231. In certain embodiments, the remote cable and the cable to the generator join within the catheter handle 231.

Figure 34A:
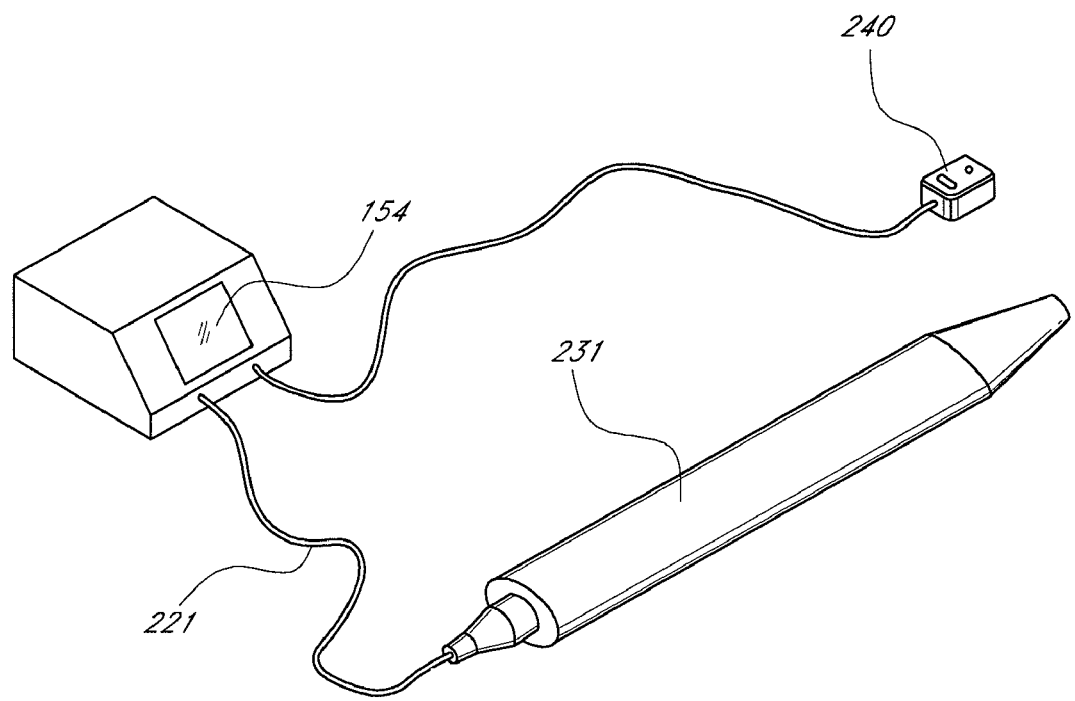
Figure 34B:
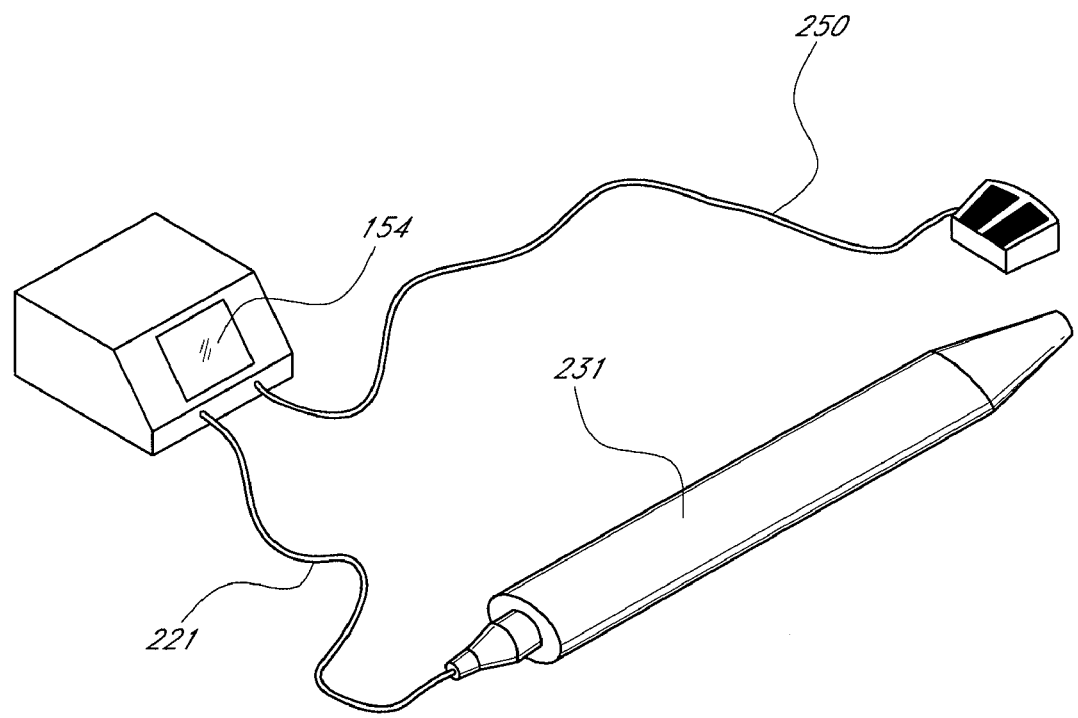

FIG. 34A illustrates yet another embodiment showing the remote switches on a separate cable 240 to the generator 154. The illustrated catheter cable 221 and catheter are separate from the remote. FIG. 34B illustrates a similar embodiment and shows a footswitch and cable 250 in place of the remote cable 240.

Figure 35:
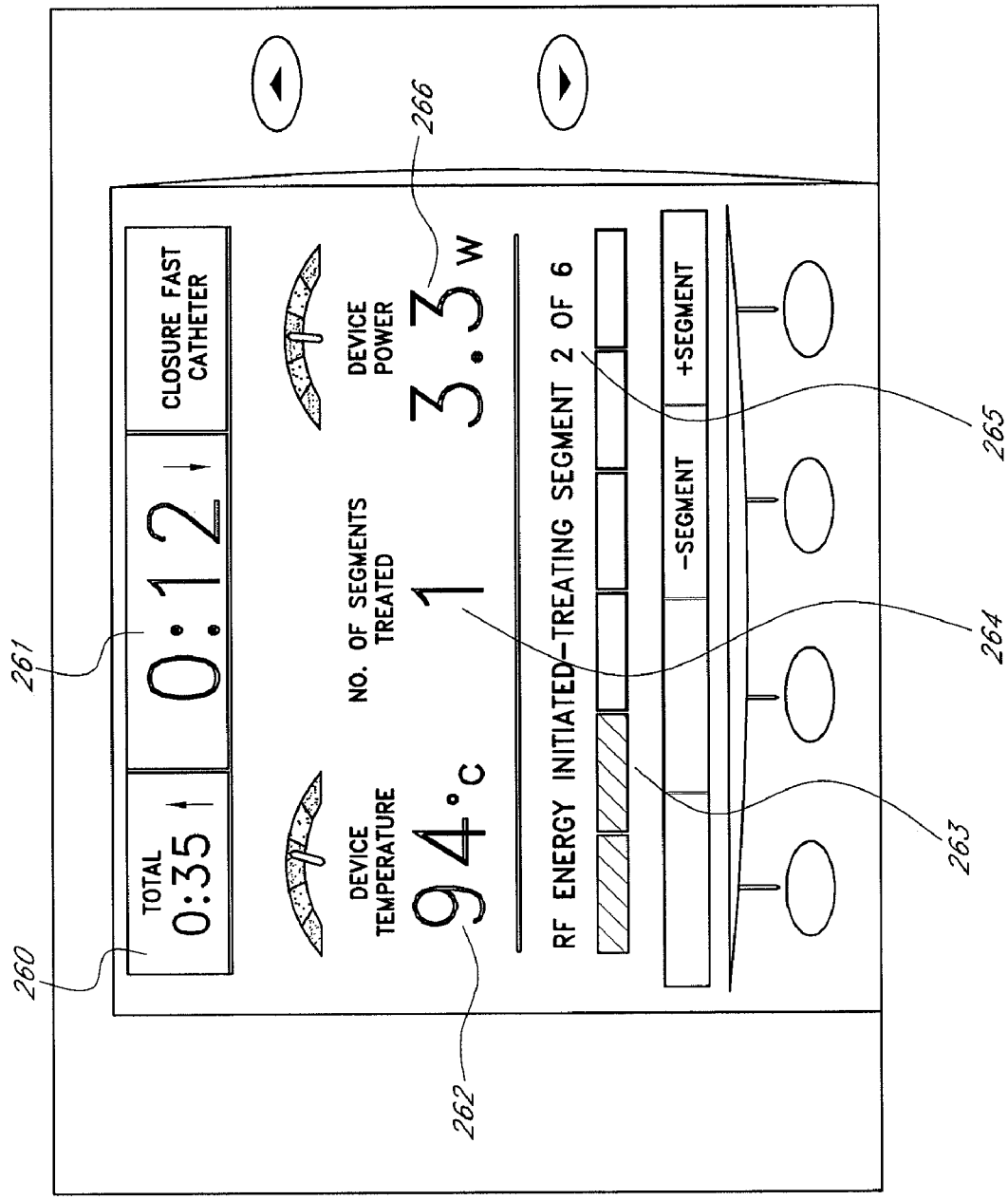
FIG. 35 illustrates a screen shot of an exemplary embodiment of a control system usable with an indexing system, according to one embodiment of the invention.
Figure 36:
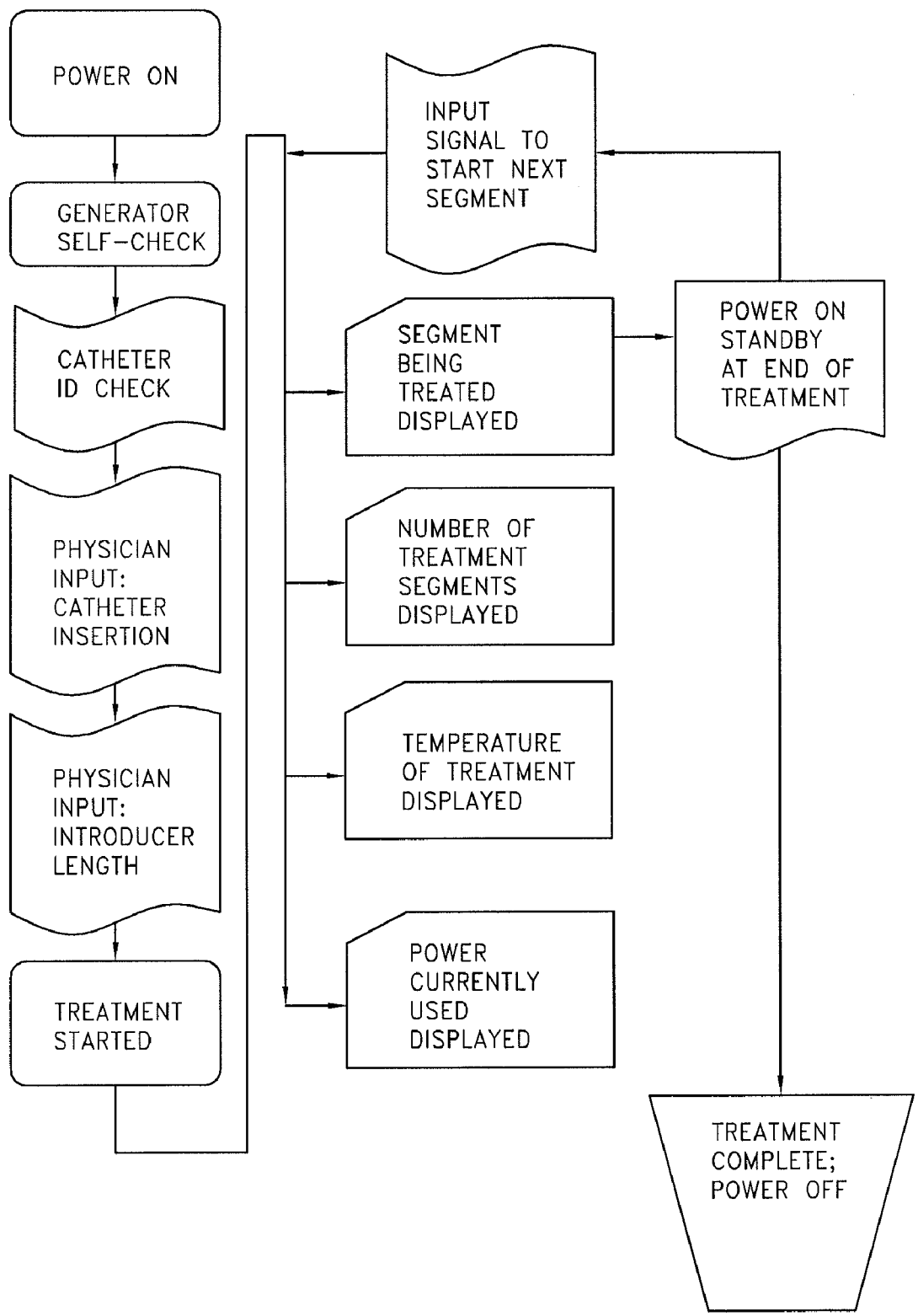
FIG. 36 illustrates a flowchart of the control system and indicates steps taken during treatment, according to one embodiment of the invention.

FIG. 35 illustrates an embodiment of an indexing system that relies on information input to a control system. In certain embodiments, the software of the control system determines the length and number of index steps based on the information from the user. The relevant information may include the length of the inserted portion of the catheter after final placement and the overall length of the introducer sheath from tip to the back end of the hub. The software determines the index step so the treatments can overlap for the total treatment of the saphenous vein starting at the SFJ and ending near the introducer sheath tip. FIG. 35 illustrates an embodiment of the information screen of the control system. The items 260 through 266 point out information which may be displayed during treatment. Item 260 indicates the elapsed time from the start of the treatment. The actual elapsed time for the specific index treatment 261, the temperature of the current treatment 262, the index step in progress of the full treatment 263, the number of index segments completed 264, the index segment currently being treated 265, and the power being used for the current index segment treatment are also shown. In certain embodiments, items 263 and 265 are determined by the controller using the physician input of the catheter inserted length and the introducer sheath length. FIG. 36 illustrates a general flowchart of the control system from the physicians' point of view and indicates the steps as they pertain to the treatment, according to one embodiment of the invention.

Methods of using an indexing HAS treatment system will now be described. The methods described herein can employ any suitable device described above or otherwise known to the skilled artisan. For example, in one embodiment, an indexing method can comprise inserting a heating element with a length of about 5 to about 7 cm into a distal-most section of an HAS to be treated. Power can then be applied to the heating element for a desired length of time to treat the segment of the HAS adjacent to the heating element. After a desired dwell time, the power supply to the heating element can be reduced or shut off. With the power off (or substantially reduced), the heating element may be indexed proximally (i.e., the heating element can be moved proximally until the distal end of the heating element is adjacent to the proximal end of the segment of the HAS that was just treated).

An example of an index treatment includes treatment at a temperature between approximately 95° C. and approximately 110° C. for a dwell time of approximately 20 seconds or less. In a more preferred embodiment, the preferred index treatment is performed at approximately 95° C. for a dwell time of approximately 20 seconds. The ramp time to temperature may be approximately 10 seconds or less, with a preferred time of approximately 5 seconds or less. The intent is to reach and maintain the treatment temperature quickly in order to apply heat to the HAS in a local manner. Once a section is treated, the distal therapeutic portion of the catheter is moved to the adjacent section. In certain embodiments, the catheter has an overlap portion of approximately 1 cm or less to substantially reduce or eliminate the number of under-treated sections or gaps as mentioned earlier. This process is repeated until the treatment of the HAS is complete. Temperatures like 110° C. at a shorter dwell time are also possible, but the depth of treatment varies.

Except as further described herein, any of the catheters disclosed herein may, in some embodiments, be similar to any of the catheters described in U.S. Pat. No. 6,401,719, issued Jun. 11, 2002, titled METHOD OF LIGATING HOLLOW ANATOMICAL STRUCTURES; or in U.S. Pat. No. 6,179,832, issued Jan. 30, 2001, titled EXPANDABLE CATHETER HAVING TWO SETS OF ELECTRODES; or in U.S. patent application Ser. No. 11/222,069, filed Sep. 8, 2005, titled METHODS AND APPARATUS FOR TREATMENT OF HOLLOW ANATOMICAL STRUCTURES. In addition, any of the catheters disclosed herein may, in certain embodiments, be employed in practicing any of the methods disclosed in the above-mentioned U.S. Pat. Nos. 6,401,719 or 6,179,832, or the above-mentioned U.S. patent application Ser. No. 11/222,069 filed Sep. 8, 2005. The entirety of each of these patents and application is hereby incorporated by reference herein and made a part of this specification.

While certain embodiments of the inventions have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions.

What is claimed is:

1. A method for use with a catheter sized for insertion into a human blood vessel, the catheter comprising an elongate shaft having a proximal end and a distal end, a heating coil having a proximal end and a distal end and being located at or near the distal end of the shaft, the heating coil being insulated so as to prevent electrical contact and electrical conduction with tissue, and a temperature sensor located along the coil near and proximal of the distal end of the coil; the method comprising:

delivering electrical power to the coil while the coil is disposed in a first treatment segment of the blood vessel;
monitoring a temperature via the temperature sensor;
moving the coil from the first treatment segment;
creating partial overlap between the first treatment segment of the blood vessel and a second treatment segment of the blood vessel by sensing a temperature drop via the temperature sensor and determining, based on the temperature drop, that the coil has been moved to the second treatment segment and that the temperature sensor has been moved, wherein the second treatment segment comprises an overlap portion created by the partial overlap between the first and second treatment segments, and a non-overlap portion adjacent to the first treatment segment and the overlap portion; and delivering electrical power to the coil again.

2. The method of claim 1, further comprising holding the coil stationary in the first treatment segment while delivering electrical power to the coil.

3. The method of claim 1, further comprising reducing or deactivating power delivery to the coil after delivering power to the coil while the coil is in the first treatment segment and before delivering power to the coil while the coil is in the second treatment segment.

4. The method of claim 1, wherein a portion of the coil is disposed in the first treatment segment while delivering electrical power to the coil in the second treatment segment.

5. The method of claim 1, wherein the catheter further comprises a second temperature sensor located on the shaft proximal of the heating coil, and the method further comprises communicating an alert when sensing a temperature drop relative to body temperature at the second temperature sensor.

6. The method of claim 1, wherein the heating coil is between about 1 and about 10 centimeters in length.

7. The method of claim 6, wherein the overlap is approximately 0.5 centimeters.

8. The method of claim 1, wherein delivering power to the coil comprises delivering sufficient power to shrink or occlude the blood vessel.

9. The method of claim 8, wherein the method further comprises using a display to symbolically represent which treatment segment is being treated with the coil.

10. The method of claim 9, wherein the display comprises an alphanumeric display.

11. The method of claim 9, wherein using the display comprises indicating the treatment segment in progress of a total number of treatment segments to be treated.

12. The method of claim 9, wherein using the display comprises indicating the number of treatment segments that have been treated.

13. An apparatus comprising:
a catheter sized for insertion into a human blood vessel, the catheter comprising an elongate shaft having a proximal end and a distal end, a heating coil having a proximal end and a distal end and being located at or near the distal end of the shaft, the heating coil being insulated so as to prevent electrical contact and electrical conduction with tissue, and a temperature sensor located along the coil near and proximal of the distal end of the coil;
a display; and
a controller electrically connected to the catheter and the display, the controller configured to:
deliver electrical power to the coil to treat a first treatment segment of the blood vessel;
monitor a temperature via the temperature sensor;
deliver electrical power to the coil again after sensing a temperature drop via the temperature sensor indicating that the coil has been moved to a second treatment segment of the blood vessel that partially overlaps the first treatment segment and also includes a non-overlapping portion adjacent to the first treatment segment;
determine the total number of treatment segments of the blood vessel, including the first and second treatment segments; and
provide a signal to the display allowing the display to indicate symbolically which of the treatment segments have been and/or are currently being treated with the coil.

14. The apparatus of claim 13, wherein the controller is further configured to reduce or deactivate power delivery to the coil after delivering power to the coil while the coil is in the first treatment segment and before delivering power to the coil while the coil is in the second treatment segment.

15. The apparatus of claim 13, wherein the catheter further comprises a second temperature sensor located on the shaft proximal of the heating coil, and the controller is further configured to communicate an alert when sensing a temperature drop relative to body temperature at the second temperature sensor.

16. The apparatus of claim 13, wherein the heating coil is between about 1 and about 10 centimeters in length.

17. The apparatus of claim 16, wherein the overlap is approximately 0.5 centimeters.

18. The apparatus of claim 13, wherein the display comprises an alphanumeric display.

19. The apparatus of claim 13, wherein the display indicates the treatment segment in progress of a total number of treatment segments to be treated.

20. The apparatus of claim 13, wherein the display indicates how many treatment segments have been completed.

21. The apparatus of claim 13, wherein the heating coil comprises an elongate element that is configured such that, when the elongate element is in a coiled configuration, adjacent turns of the coil are not in electrical contact with one another.

22. The apparatus of claim 21, wherein the catheter further comprises an insulating tube surrounding the outside of the coil.

23. An apparatus comprising:
a catheter sized for insertion into a human blood vessel, the catheter comprising an elongate shaft having a proximal end and a distal end, a heating coil having a proximal end and a distal end and being located at or near the distal end of the shaft, the heating coil being insulated so as to prevent electrical contact and electrical conduction with tissue, and a temperature sensor;
a display; and
a controller electrically connected to the catheter and the display, the controller configured to:
indicate on the display a first treatment segment of the blood vessel;
deliver electrical power to the coil to treat the first treatment segment of the blood vessel;
monitor a temperature via the temperature sensor;
distinguish the first treatment segment of the blood vessel from a second treatment segment of the blood vessel that partially overlaps the first treatment segment and also includes a non-overlapping portion adjacent to the first treatment segment;
indicate on the display the second treatment segment of the blood vessel; and
deliver electrical power to the coil again after sensing a temperature via the temperature sensor and after the coil has been moved to the second treatment segment of the blood vessel.

24. The apparatus of claim 23, wherein the controller is further configured to sense a temperature drop via the temperature sensor indicating that the coil has been moved to the second treatment segment of the blood vessel.

25. The apparatus of claim 24, wherein the controller is further configured to distinguish the first treatment segment of the blood vessel from the second treatment segment of the blood vessel by sensing the temperature drop via the temperature sensor indicating that the coil has been moved to the second treatment segment of the blood vessel.

26. The apparatus of claim 24, wherein the controller is further configured to distinguish the first treatment segment of the blood vessel from the second treatment segment of the blood vessel by using an indexing system.

27. The apparatus of claim 24, wherein the controller is further configured to distinguish the first treatment segment of the blood vessel from the second treatment segment of the blood vessel by using an indexing system that determines the length and number of index steps.

* * * * *